United States Patent
Hirohara et al.

(10) Patent No.: US 7,270,413 B2
(45) Date of Patent: Sep. 18, 2007

(54) OPHTHALMIC DATA MEASURING APPARATUS, OPHTHALMIC DATA MEASUREMENT PROGRAM AND EYE CHARACTERISTIC MEASURING APPARATUS

(75) Inventors: Yoko Hirohara, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 210 days.

(21) Appl. No.: 10/544,229

(22) PCT Filed: Jan. 29, 2004

(86) PCT No.: PCT/JP2004/000794

§ 371 (c)(1),
(2), (4) Date: Sep. 2, 2005

(87) PCT Pub. No.: WO2004/069044

PCT Pub. Date: Aug. 19, 2004

(65) Prior Publication Data

US 2006/0170865 A1 Aug. 3, 2006

(30) Foreign Application Priority Data

Feb. 3, 2003 (JP) ............................. 2003-025428
May 13, 2003 (JP) ............................. 2003-134829

(51) Int. Cl.
*A61B 3/10* (2006.01)
*A61B 3/00* (2006.01)
(52) U.S. Cl. ..................... 351/205; 351/211; 351/212; 351/221; 351/246
(58) Field of Classification Search ............... 351/205, 351/206, 210, 211, 221, 246
See application file for complete search history.

(56) References Cited

U.S. PATENT DOCUMENTS 6,905,209 B2 * 6/2005 Mihashi et al. ............. 351/221
7,216,980 B2 * 5/2007 Mihashi et al. ............. 351/205

FOREIGN PATENT DOCUMENTS

JP 2001-120504 A 5/2001
JP 2002-306416 A 10/2002
JP 2002-306417 A 10/2002

OTHER PUBLICATIONS

Peter G.J. Barten, "Contrast Sensitivity of the Human Eye and Its Effects on Image Quality," SPIE Optical Engineering Press, 1999, pp. 27-66.
Wilson S. Geisler, "Sequential Ideal-Observer Analysis of Visual Discriminations," Psychological Review, 1989, vol. 96, No. 2, pp. 267-314.

* cited by examiner

*Primary Examiner*—Ricky Mack
*Assistant Examiner*—Jack Dinh
(74) *Attorney, Agent, or Firm*—Foley & Lardner LLP

(57) ABSTRACT

It is possible to estimate optical characteristic according to a pupil diameter in daily life of an examinee, correction data near to the optimal prescription value, eyesight, and sensitivity. A calculation section receives measurement data indicating refractive power distribution of an eye to be examined and pupil data on the eye and calculates lower order and higher order aberrations according to the measurement data and the pupil data (S101 to 105). For example, a pupil edge is detected from the anterior ocular segment image and a pupil diameter is calculated. By using this pupil diameter, lower order and higher order aberrations are calculated. According to the lower order and higher order aberrations obtained, the calculation section performs simulation of a retina image by using high contrast or low contrast target and estimates the eyesight by comparing the result to a template and/or obtains sensitivity (S107). Alternatively, according to the lower order and the higher order aberrations obtained, the calculation section calculates an evaluation parameter indicating the quality of visibility by the eye to be examined such as the Strehl ratio, the phase shift (PTF), and the visibility by comparison of the retina image simulation with the template. According to the evaluation parameter calculated, the calculation section changes the lower order aberration amount so as to calculate appropriate correction data for the eye to be examined (S107). The calculation section outputs data such as the eyesight, sensitivity, correction data, and the simulation result to a memory or a display section (S109).

27 Claims, 32 Drawing Sheets

LANDOLT'S RING
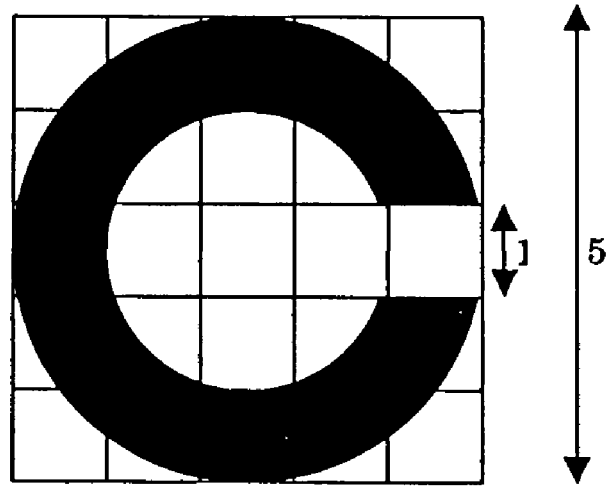
HIGH CONTRAST
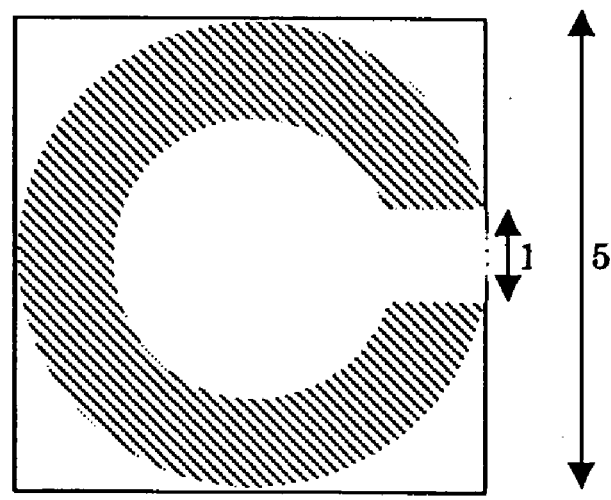
LOW CONTRAST
FIG.3

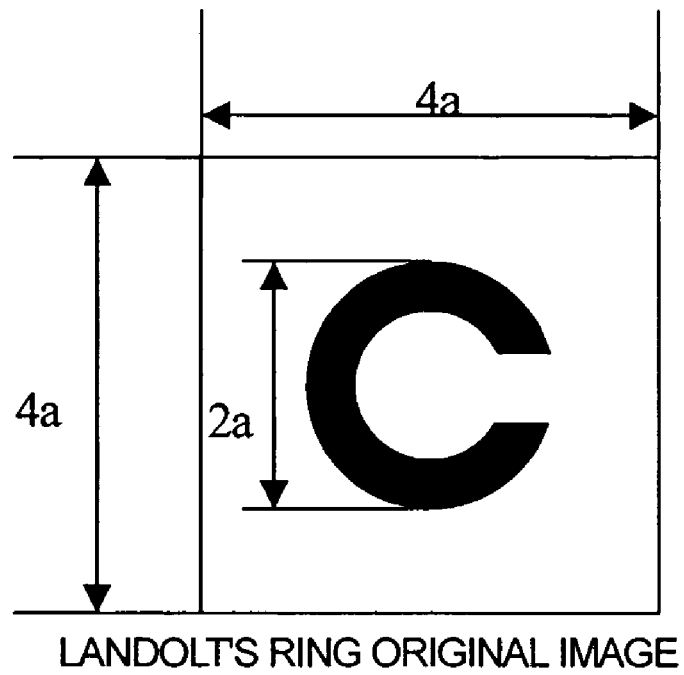
LANDOLT'S RING ORIGINAL IMAGE
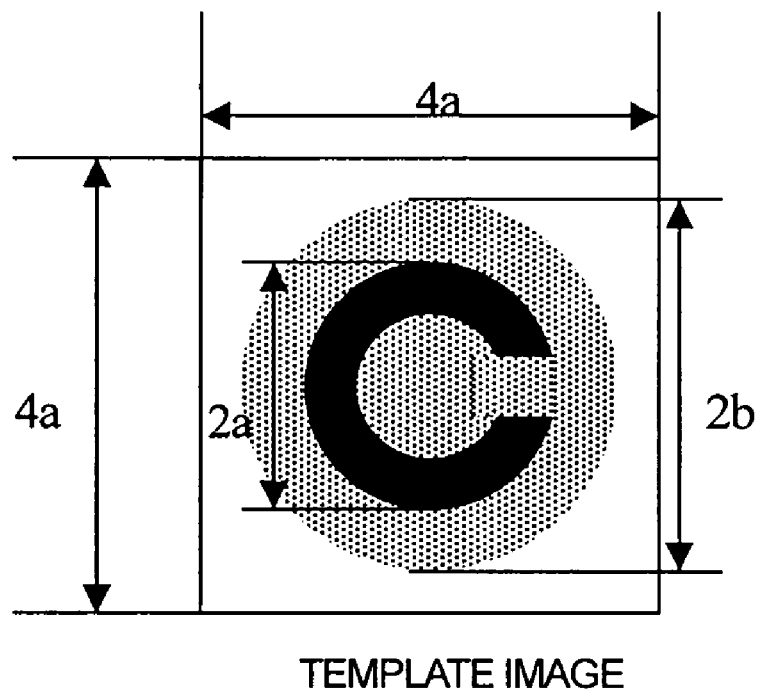
TEMPLATE IMAGE
FIG.9

PRESCRIPTION DATA FOR EYEGLASSES/CONTACTS

PUPIL DIAMETER IN THE DAYTIME: 3.42 mm

|   | CORRECTION DATA | COMPENSATION CORRECTION DATA |
|---|---|---|
| S | -7.00 | -7.15 |
| C | -0.5 | -0.35 |
| A | 3 | 5 |
| CORRECTED VISUAL ACUITY | 1.2 | 1.5 |

FIG.18

PRESCRIPTION DATA FOR REFRACTIVE SURGERY

PUPIL DIAMETER IN THE DAYTIME: 3.42 mm

| | MEASURED VALUE | COMPENSATION CORRECTION DATA | PREDICTED VALUE AFTER COMPENSATION CORRECTION |
|---|---|---|---|
| S | -7.00 | -7.15 | -0.15 |
| C | 0.5 | 0.35 | 0.15 |
| A | 3 | 5 | 4 |
| HIGHER ORDER SPHERICAL ABERRATION | 0.125 | | 0.280 |
| HIGHER ORDER ASTIGMATIC ABERRATION | 0.105 | | 0.125 |
| HIGHER ORDER COMA ABERRATION | 0.085 | | 0.090 |
| CORRECTED VISUAL ACUITY | 1.2 | 2.0 (IDEAL VALUE) | 1.5 |

FIG. 19

PRESCRIPTION DATA FOR EYEGLASSES/CONTACTS
(COMPARISON WHEN ENVIRONMENTAL CONDITION IS CHANGED)

| ENVIRONMENTAL CONDITION: PUPIL DIAMETER | IN THE DAYTIME: 3.42mm | | UNDER FLUORESCENT LAMP: 6.54mm | | IN ROOM AND DAYTIME: 4.35 mm | |
|---|---|---|---|---|---|---|
| | CORRECTION DATA | COMPENSATION CORRECTION DATA | CORRECTION DATA | COMPENSATION CORRECTION DATA | CORRECTION DATA | COMPENSATION CORRECTION DATA |
| S | -7.00 | -7.15 | -7.33 | -7.43 | -7.18 | -7.31 |
| C | -0.5 | -0.35 | -0.40 | -0.45 | -0.45 | -0.38 |
| A | 3 | 5 | 4 | 4 | 3 | 4 |
| CORRECTED VISUAL ACUITY | 1.2 | 1.5 | 1.0 | 1.2 | 1.2 | 1.2 |

VISIBILITY OF LANDOLT'S RING (0.5)

FIG.20

PUPIL DATA
(COMPARISON WHEN ENVIRONMENTAL CONDITION IS CHANGED)

| ENVIRONMENTAL CONDITION: PUPIL DIAMETER | | IN THE DAYTIME: 3.42 mm | UNDER FLUORESCENT LAMP: 6.54 mm | IN ROOM AND DAYTIME: 4.35 mm |
|---|---|---|---|---|
| SHIFT AMOUNT FROM LIMBUS CENTER (mm) | x | 0.542 | 0.723 | 0.601 |
| | y | 0.109 | 0.120 | 0.110 |
| CORRECTED VISUAL ACUITY | | 1.5 | 1.2 | 1.2 |

FIG.21

PRESCRIPTION DATA FOR EYEGLASSES/CONTACTS
(COMPARISON TO CONSTANT PUPIL DIAMETER)

| ENVIRONMENTAL CONDITION: PUPIL DIAMETER | 4mm | | 6mm | | AT TIME OF MEASUREMENT (50 lx): 6.45 mm | |
|---|---|---|---|---|---|---|
| | CORRECTION DATA | COMPENSATION CORRECTION DATA | CORRECTION DATA | COMPENSATION CORRECTION DATA | CORRECTION DATA | COMPENSATION CORRECTION DATA |
| S | -7.03 | -7.18 | -7.30 | -7.45 | -7.33 | -7.43 |
| C | -0.52 | -0.41 | -0.40 | -0.43 | -0.40 | -0.45 |
| A | 3 | 5 | 4 | 5 | 4 | 4 |
| CORRECTED VISUAL ACUITY | 1.2 | 1.5 | 1.0 | 1.2 | 0.9 | 1.0 |

VISIBILITY OF LANDOLT'S RING (0.5)

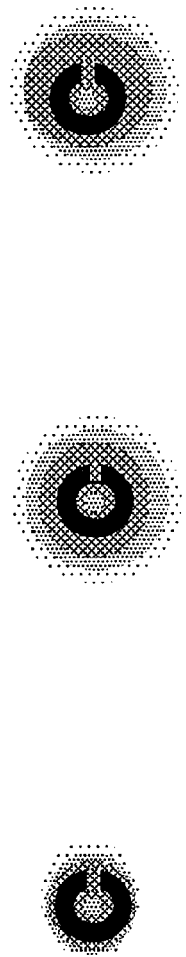

FIG.22

PRESCRIPTION DATA FOR EYEGLASSES/CONTACTS

PUPIL DIAMETER IN THE DAYTIME: 3.42 mm

|   | CORRECTION DATA | COMPENSATION CORRECTION DATA |
|---|---|---|
| S | −7.00 | −7.15 |
| C | −0.5 | −0.35 |
| A | 3 | 5 |
| Strehl RATIO | 0.088 | 0.122 |

FIG.29

PRESCRIPTION DATA FOR REFRACTIVE SURGERY

PUPIL DIAMETER IN THE DAYTIME: 3.42 mm

|  | MEASURED VALUE | COMPENSATION CORRECTION DATA | PREDICTED VALUE AFTER COMPENSATION CORRECTION |
|---|---|---|---|
| S | -7.00 | -7.15 | -0.15 |
| C | 0.5 | 0.35 | 0.15 |
| A | 3 | 5 | 4 |
| HIGHER ORDER SPHERICAL ABERRATION | 0.125 | | 0.280 |
| HIGHER ORDER ASTIGMATIC ABERRATION | 0.105 | | 0.125 |
| HIGHER ORDER COMA ABERRATION | 0.085 | | 0.090 |
| Strehl RATIO | 0.088 | 0.252 (IDEAL VALUE) | 0.198 |

FIG.30

PRESCRIPTION DATA FOR EYEGLASSES/CONTACTS
(COMPARISON WHEN ENVIRONMENTAL CONDITION IS CHANGED)

| ENVIRONMENTAL CONDITION: PUPIL DIAMETER | IN THE DAYTIME: 3.42mm | | UNDER FLUORESCENT LAMP: 6.54mm | | IN ROOM AND DAYTIME 4.35 mm | |
|---|---|---|---|---|---|---|
| | CORRECTION DATA | COMPENSATION CORRECTION DATA | CORRECTION DATA | COMPENSATION CORRECTION DATA | CORRECTION DATA | COMPENSATION CORRECTION DATA |
| S | -7.00 | -7.15 | -7.33 | -7.43 | -7.18 | -7.31 |
| C | -0.5 | -0.35 | -0.40 | -0.45 | -0.45 | -0.38 |
| A | 3 | 5 | 4 | 4 | 3 | 4 |
| Strehl RATIO | 0.088 | 0.122 | 0.056 | 0.076 | 0.078 | 0.095 |

VISIBILITY OF LANDOLT'S RING (0.5)

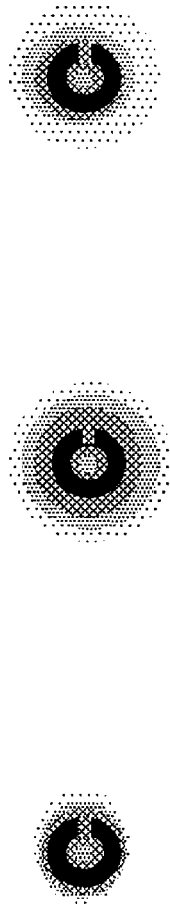

FIG.31

PRESCRIPTION DATA FOR EYEGLASSES/CONTACTS
(COMPARISON TO CONSTANT PUPIL DIAMETER)

| ENVIRONMENTAL CONDITION: PUPIL DIAMETER | 4mm | | 6mm | | AT TIME OF MEASUREMENT (50 lx): 6.45 mm | |
|---|---|---|---|---|---|---|
| | CORRECTION DATA | COMPENSATION CORRECTION DATA | CORRECTION DATA | COMPENSATION CORRECTION DATA | CORRECTION DATA | COMPENSATION CORRECTION DATA |
| S | -7.03 | -7.18 | -7.30 | -7.45 | -7.33 | -7.43 |
| C | -0.52 | -0.41 | -0.40 | -0.43 | -0.40 | -0.45 |
| A | 3 | 5 | 4 | 5 | 4 | 4 |
| Strehl RATIO | 0.086 | 0.120 | 0.064 | 0.079 | 0.056 | 0.076 |

VISIBILITY OF LANDOLT'S RING (0.5)

OPHTHALMIC DATA MEASURING APPARATUS, OPHTHALMIC DATA MEASUREMENT PROGRAM AND EYE CHARACTERISTIC MEASURING APPARATUS

TECHNICAL FIELD

The present invention relates to an ophthalmic data measuring apparatus for measuring appropriate correction data and/or estimating visual acuity in daily life, an ophthalmic data measurement program and an eye characteristic measuring apparatus.

BACKGROUND ART

Conventionally, as a technique for measuring ocular correction data, measurement of S (Sphere), C (Cylinder) and A (axis) by a refractometer has been carried out. Besides, recently, an eye characteristic measuring apparatus capable of measuring higher order aberrations has also been developed, and not only S, C and A on a line like, for example, a ring of φ3 mm as in a refractometer, but also S, C and A on a plane when a pupil diameter is made various sizes can be calculated from lower order aberrations. By the eye characteristic measuring apparatus like this, especially after a refraction correcting surgical operation or in an eye disease, values closer to prescription values of eyeglasses or contact lenses than the refractometer can be calculated (for example, see JP-A-2002-204785, JP-A-2002-209854, JP-A-2002-306416, JP-A-2002-306417, etc.).

Besides, as an apparatus for displaying the visibility of a subjective eye at the time of correction or by the eye, an apparatus by the present applicant is disclosed (for example, see JP-A-2001-120504, JP-A-7-100107). In these apparatuses, for example, the visibility of a predetermined index is displayed on display means based on the measured optical characteristic of the eye to be examined (eye to be measured).

DISCLOSURE OF THE INVENTION

However, in the objective calculation results of the conventional eye characteristic measuring apparatus and prescription values of eyeglasses, contacts, or the like, there is a case where a difference from an appropriate value occurs, and there has been a case where they are insufficient as evaluation of S, C and A. Besides, conventionally, since a measurement is made using a fixed value as the pupil diameter of an eye to be examined, there has been a case where an appropriate prescription value corresponding to the pupil diameter of the eye to be examined can not be obtained.

Besides, in the conventional measurement, although the visibility of an index or the like is displayed, the visual acuity of the subjective eye is not estimated. Further, the prediction of the visibility is often the visibility under a generally used visual acuity measurement condition, and the visibility and the visual acuity under an environment of the eye to be examined, for example, in daily life, have not been obtained.

Besides, conventionally, when PSF or MTF on the retina is simply evaluated, there has been a case where it is very difficult to obtain an appropriate evaluation, that is, a value close to a subjective test.

In view of the above, the invention has an object to calculate an optical characteristic corresponding to a pupil diameter of an eye to be examined and correction data close to an optimum prescription value and to perform more accurate measurement.

Besides, according to an object of the invention, in the measurement results of an eye characteristic measuring apparatus which can measure higher order aberrations, in the case where a higher order aberration is included, a lower order aberration corresponding to the time of objective complete correction is not made compensation correction data, optical performance is evaluated with, for example, a Strehl ratio or a phase shift, a lower order aberration amount by which the Strehl ratio becomes large and/or the phase shift becomes small is calculated, and compensation correction data of S, C, A and the like at that time is obtained, so that correction data close to the optimum prescription value of eyeglasses/contacts is obtained.

Further, an object is to obtain correction data close to a subjective value by performing simulation of visibility of an index for eye examination to obtain an appropriate correction element.

The invention has an object to estimate visual acuity of an eye to be examined in luminance corresponding to an environment of a subjective eye in daily life (for example, in the daytime or in a room). Besides, the invention has an object to estimate visual acuity with respect to an index of high contrast and/or low contrast in view of a pupil diameter of an eye to be examined in daily life. The invention has an object to predict contrast sensitivity in view of a pupil diameter. Besides, the invention has also an object according to which a pupil diameter in luminance corresponding to an environment of a subjective eye is used, correction data close to an optimum prescription value under the environment is obtained, and the visual acuity under the environment of the subjective eye at the time of correction by the obtained correction data is estimated. Besides, the simulation of an index, such as a Landolt's ring, on the retina in view of the size of a pupil area calculated in the middle of the process is also singly effective.

According to the first solving means of this invention, there is provided, an ophthalmic data measuring apparatus comprising:

a first light source part to emit a light flux of a first wavelength;

a first illuminating optical system for performing illumination to condense the light flux from the first light source part on a vicinity of a retina of an eye to be examined;

a first light receiving optical system for receiving a part of the light flux reflected by and returning from the retina of the eye to be examined through a first conversion member to convert it into at least substantially 17 beams;

a first light receiving part for receiving the received light flux of the first light receiving optical system; and a calculation section to perform Zernike analysis based on an inclination angle of the light flux obtained by the first light receiving part, to obtain an optical characteristic of the eye to be examined, and (1) to estimate one of or two or more of a visual acuity, the optical characteristic and a sensitivity of the eye to be examined under an observation condition corresponding to an environment of the eye to be examined, or (2) to calculate appropriate correction data suitable for the eye to be examined, wherein the calculation section comprises:

first means for obtaining measurement data indicating a refractive power distribution of the eye to be examined and pupil data including a value of a pupil diameter of the eye to be examined or a pupil diameter image and for obtaining lower order aberrations and higher order aberrations based on an observation condition parameter including the measurement data and the pupil data;

second means for calculating an evaluation parameter indicating quality of visibility by the eye to be examined based on the observation condition parameter and/or the obtained lower order aberrations and the higher order aberrations; and third means for, in accordance with the calculated evaluation parameter, (1) estimating one of or two or more of the visual acuity, the optical characteristic and the sensitivity, of the eye to be examined under the observation condition corresponding to the environment of a subjective eye or (2) calculating the appropriate correction data suitable for the eye to be examined by changing the lower order aberration.

According to the second solving means of this invention, there is provided, an ophthalmic data measurement program for causing a computer to execute:

a first step at which a calculation section obtains measurement data indicating a refractive power distribution of an eye to be examined and pupil data including a value of a pupil diameter of the eye to be examined or a pupil diameter image, and obtains lower order aberrations and higher order aberrations based on an observation condition parameter including the measurement data and the pupil data;

a second step at which the calculation section calculates an evaluation parameter indicating quality of visibility by the eye to be examined based on the observation condition parameter and/or the obtain lower order aberrations and the higher order aberrations; and a third step at which in accordance with the calculated evaluation parameter, the calculation section estimates one of or two or more of a visual acuity, an optical characteristic and a sensitivity of the eye to be examined under an observation condition corresponding to an environment of a subjective eye, or calculates appropriate correction data suitable for the eye to be examined by changing the lower order aberration.

According to the third solving means of this invention, there is provided, an ophthalmic data measurement program for causing a computer to execute:

a first step at which a calculation section receives measurement data indicating a refractive power distribution of an eye to be examined, and obtains lower order aberrations and higher order aberrations based on the measurement data;

a second step at which the calculation section calculates an evaluation parameter indicating quality of visibility by the eye to be examined based on the obtained lower order aberrations and the higher order aberrations; and a third step at which the calculation section calculates appropriate correction data suitable for the eye to be examined by changing the lower order aberration in accordance with the calculated evaluation parameter.

According to the fourth solving means of this invention, there is provided, an eye characteristic measuring apparatus comprising:

a first light source part to emit a light flux of a first wavelength;

a first illuminating optical system for performing illumination to condense the light flux from the first light source part on a vicinity of a retina of an eye to be examined;

a first light receiving optical system for receiving a part of the light flux reflected by and returning from the retina of the eye to be examined through a first conversion member to convert it into at least substantially 17 beams;

a first light receiving part for receiving the received light flux of the first light receiving optical system; and a calculation section for receiving pupil data including a pupil image of the eye to be examined in a measurement environment, calculating a pupil diameter under the measurement environment based on the received pupil data, and obtaining an optical characteristic of the eye to be examined based on the calculated pupil diameter and an output signal from the first light receiving part.

BRIEF DESCRIPTION OF THE DRAWINGS

FIG. 3 is an explanatory view of a Landolt's ring.

FIG. 9 is an explanatory view of template matching.

FIG. 18 is an explanatory view of an example of prescription data for eyeglasses/contacts.

FIG. 19 is an explanatory view of an example of data for refractive surgery.

FIG. 20 is an explanatory view of an example of prescription data for eyeglasses/contacts when an environmental condition is changed.

FIG. 21 is an explanatory view of an example of pupil data when an environmental condition is changed.

FIG. 22 is a comparison view of prescription data for eyeglasses/contacts with respect to measurement with a constant pupil diameter.

FIG. 29 is an explanatory view of an example of prescription data for eyeglasses/contacts.

FIG. 30 is an explanatory view of an example of data for refractive surgery.

FIG. 31 is an explanatory view of an example of prescription data for eyeglasses/contacts when an environmental condition is changed.

BEST MODE FOR CARRYING OUT THE INVENTION

Figure 1:
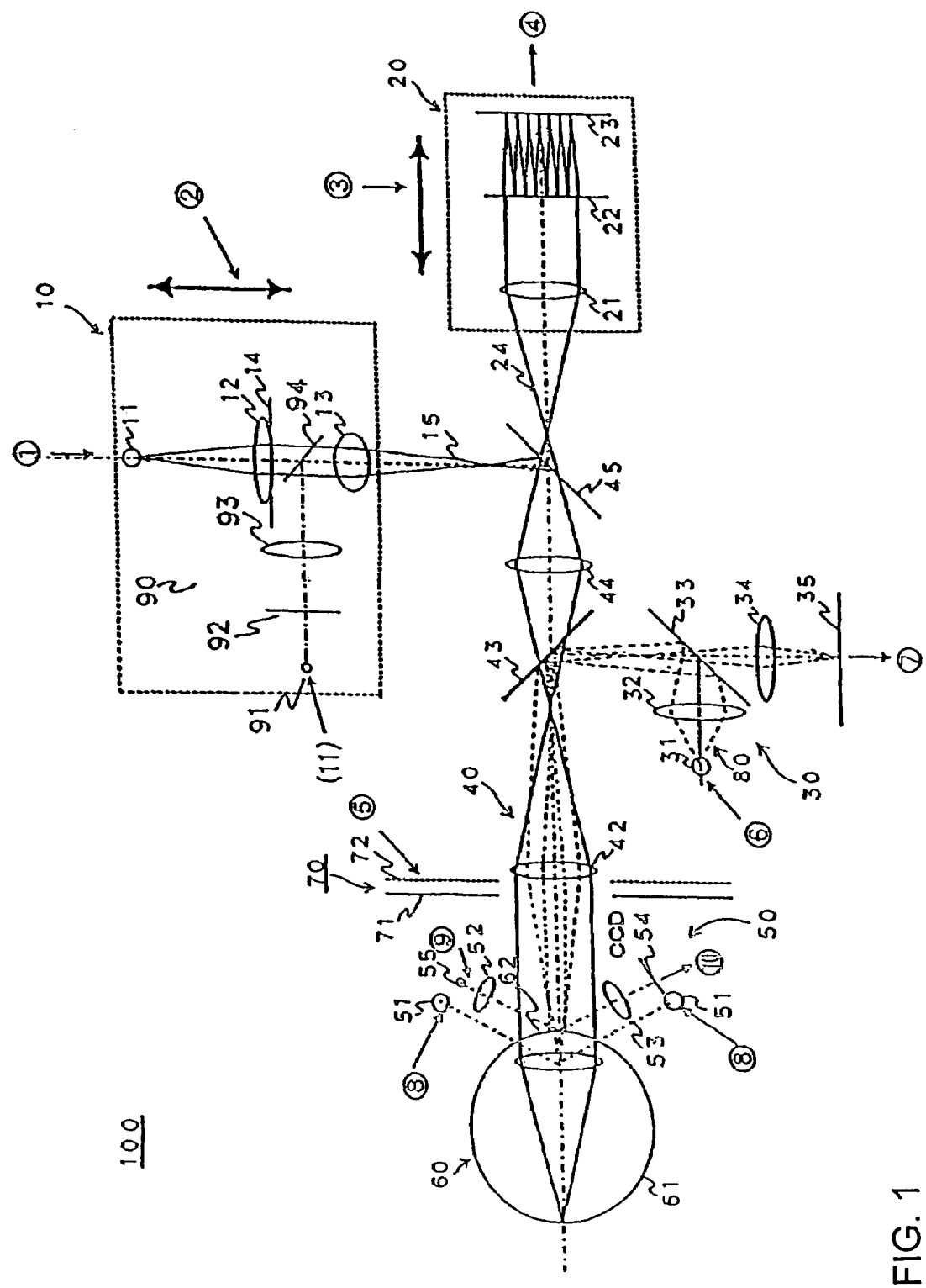
FIG. 1 is a structural view of an optical system 100 of an eye optical characteristic measuring apparatus.

FIG. 1 is a structural view of an optical system 100 of an eye optical characteristic measuring apparatus (an ophthalmic data measuring apparatus).

The optical system 100 of the eye optical characteristic measuring apparatus is an apparatus for measuring an optical characteristic of an eye 60 to be measured as an object, and includes a first illuminating optical system 10, a first light receiving optical system 20, a second light receiving optical system 30, a common optical system 40, an adjusting optical system 50, a second illuminating optical system 70, and a second light sending optical system 80. Incidentally, with respect to the eye 60 to be measured, a retina 61 and a cornea 62 are shown in the drawing.

The first illuminating optical system 10 includes, for example, a first light source part 11 for emitting a light flux of a first wavelength, and a condensing lens 12, and is for illuminating a minute area on the retina (retina) 61 of the eye 60 to be measured with the light flux from the first light source part 11 so that its illumination condition can be suitably set. Incidentally, here, as an example, the first wavelength of the illuminating light flux emitted from the first light source part 11 is a wavelength (for example, 780 nm) of an infrared range.

Besides, it is desirable that the first light source part 11 has a high spatial coherence and a low temporal coherence. Here, the first light source part 11 is, for example, a super luminescence diode (SLD), and a point light source having high luminescence can be obtained. Incidentally, the first light source part 11 is not limited to the SLD, and for example, a laser having a high spatial coherence and a high temporal coherence can also be used by inserting a rotation diffused plate or declination prism (D prism) or the like to suitably lower the temporal coherence. Further, an LED having a low spatial coherence and a low temporal coherence can also be used, if light quantity is sufficient, by inserting, for example, a pinhole or the like at a position of a light source in an optical path.

The first light receiving optical system 20 includes, for example, a collimator lens 21, a Hartmann plate 22 as a conversion member for converting a part of a light flux (first light flux) reflected and returned from the retina 61 of the eye 60 to be measured into at least 17 beams, and a first light receiving part 23 for receiving the plural beams converted by the Hartmann plate 22, and is for guiding the first light flux to the first light receiving part 23. Besides, here, a CCD with little readout noise is adopted for the first light receiving part 23, and as the CCD, a suitable type of CCD, for example, a general low noise type of CCD, a cooling CCD of 1000*1000 elements for measurement, or the like is applicable.

The second illuminating optical system 70 includes a second light source 72 and a Placido's disk 71. Incidentally, the second light source 72 can be omitted. The Placido's disk (PLACIDO'S DISK) 71 is for projecting an index of a pattern composed of plural co-axial rings. Incidentally, the index of the pattern composed of the plural co-axial rings is an example of an index of a specified pattern, and a different suitable pattern can be used. Then, after an alignment adjustment described later is completed, the index of the pattern composed of the plural co-axial rings can be projected.

The second light sending optical system 80 is for mainly performing, for example, the alignment adjustment described later, and measurement and adjustment of a coordinate origin and a coordinate axis, and includes a second light source part 31, a condensing lens 32, and a beam splitter 33.

The second light receiving optical system 30 includes a condensing lens 34 and a second light receiving part 35. The second light receiving optical system 30 guides a light flux (second light flux), which is originated from the pattern of the Placido's disk 71 illuminated from the second illuminating optical system 70 and is reflected and returned from the anterior eye part or the cornea 62 of the eye 60 to be measured, to the second light receiving part 35. Besides, it can also guide a light flux, which is emitted from the second light source part 31 and is reflected and returned from the cornea 62 of the eye 60 to be measured, to the second light receiving part 35. Incidentally, as the second wavelength of the light flux emitted from the second light source part 31, for example, a wavelength different from the first wavelength (here, 780 nm) and longer (for example, 940 nm) than that can be selected.

The common optical system 40 is disposed on an optical axis of the light flux emitted from the first illuminating optical system 10, can be included in the first and the second illuminating optical systems 10 and 70, the first and the second light receiving optical systems 20 and 30, the second light sending optical system 80 and the like in common, and includes, for example, an afocal lens 42, beam splitters 43 and 45, and a condensing lens 44. The beam splitter 43 is formed of such a mirror (for example, a dichroic mirror) that the wavelength of the second light source part 31 is sent (reflected) to the eye 60 to be measured, and the second light flux reflected and returned from the retina 61 of the eye 60 to be measured is reflected, and on the other hand, the wavelength of the first light source part 11 is transmitted. The beam splitter 45 is formed of such a mirror (for example, a polarization beam splitter) that the light flux of the first light source part 11 is sent (reflected) to the eye 60 to be measured, and the first light flux reflected and returned from the retina 61 of the eye 60 to be measured is transmitted. By the beam splitters 43 and 45, the first and the second light fluxes do not mutually enter the other optical systems to generate noise.

The adjusting optical system 50 is for mainly performing, for example, a working distance adjustment described later, includes a third light source part 51, a fourth light source part 55, condensing lenses 52 and 53, and a third light receiving part 54, and is for mainly performing the working distance adjustment.

A third illuminating optical system 90 includes an optical path for projection of an index for causing, for example, fixation of the eye 60 to be measured or fogging, and includes a fifth light source part (for example, a lamp) 91, a fixation target 92 and a relay lens 93. The fixation target 92 can be irradiated to the retina 61 by the light flux from the fifth light source part 91, and the eye 60 to be measured is made to observe its image. The fixation target 92 and the retina 61 are put in a conjugated relation by the third illuminating optical system 90. Besides, the fifth light source part 91 is also a light source (anterior ocular segment illuminating part) to illuminate the anterior ocular segment of the eye 60 to be measured under different luminance conditions. The light amount of the fifth light source part 91 is adjusted, so that the illumination state of the eye 60 to be measured is changed and the size of the pupil can be changed. Incidentally, as the anterior ocular segment illuminating part, in addition to the fifth light source part 91, an appropriate light source such as the second light source 72 may be used.

Next, the alignment adjustment will be described. The alignment adjustment is mainly carried out by the second light receiving optical system 30 and the second light sending optical system 80.

First, the light flux from the second light source part 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux such as is emitted from a point at the half of the radius of curvature of the cornea 62. The divergence light flux is received as a spot image by the second light receiving part 35 through the afocal lens 42, the beam splitters 43 and 33, and the condensing lens 34.

Here, in the case where the spot image on the second light receiving part 35 is outside the optical axis, the main body of the eye optical characteristic measuring apparatus is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the eye 60 to be measured is illuminated by the third light source part 51, and an image of the eye 60 to be measured obtained by this illumination is formed on the second light receiving part 35, and accordingly, this image may be used to make the pupil center coincide with the optical axis.

Next, the working distance adjustment will be described. The working distance adjustment is mainly carried out by the adjusting optical system 50.

First, the working distance adjustment is carried out by, for example, irradiating the eye 60 to be measured with a parallel light flux emitted from the fourth light source part 55 and close to the optical axis, and by receiving the light reflected from the eye 60 to be measured through the condensing lenses 52 and 53 by the third light receiving part 54. Besides, in the case where the eye 60 to be measured is in a suitable working distance, a spot image from the fourth light source part 55 is formed on the optical axis of the third light receiving part 54. On the other hand, in the case where the eye 60 to be measured goes out of the suitable working distance, the spot image from the fourth light source part 55 is formed above or below the optical axis of the third light receiving part 54. Incidentally, since the third light receiving part 54 has only to be capable of detecting a change of a light flux position on the plane containing the fourth light source part 55, the optical axis and the third light receiving part 54, for example, a one-dimensional CCD arranged on this plane, a position sensing device (PSD) or the like is applicable.

Next, a positional relation between the first illuminating optical system 10 and the first light receiving optical system 20 will be described.

The beam splitter 45 is inserted in the first light receiving optical system 20, and by this beam splitter 45, the light from the first illuminating optical system 10 is sent to the eye 60 to be measured, and the reflected light from the eye 60 to be measured is transmitted. The first light receiving part 23 included in the first light receiving optical system 20 receives the light transmitted through the Hartmann plate 22 as the conversion member and generates a received light signal.

Besides, the first light source part 11 and the retina 61 of the eye 60 to be measured form a conjugated relation. The retina 61 of the eye 60 to be measured and the first light receiving part 23 are conjugate. Besides, the Hartmann plate 22 and the pupil of the eye 60 to be measured form a conjugated relation. Further, the first light receiving optical system 20 forms a substantially conjugated relation with respect to the cornea 62 as the anterior eye part of the eye 60 to be measured, the pupil, and the Hartmann plate 22. That is, the front focal point of the afocal lens 42 is substantially coincident with the cornea 62 as the anterior eye part of the eye 60 to be measured and the pupil.

Besides, the first illuminating optical system 10 and the first light receiving optical system 20 are moved together so that a signal peak according to the reflected light at the light receiving part 23 becomes maximum on the condition that the light flux from the first light source part 11 is reflected at a point on which it is condensed. Specifically, the first illuminating optical system 10 and the first light receiving optical system 20 are moved in a direction in which the signal peak at the first light receiving part 23 becomes large, and are stopped at a position where the signal peak becomes maximum. By this, the light flux from the first light source part 11 is condensed on the eye 60 to be measured.

Besides, the lens 12 converts a diffused light of the light source 11 into a parallel light. A diaphragm 14 is positioned at an optically conjugated position with respect to the pupil of the eye or the Hartmann plate 22. The diaphragm 14 has a diameter smaller than an effective range of the Hartmann plate 22, and the so-called single path aberration measurement (method in which aberrations of an eye have an influence on only the light receiving side) is established. In order to satisfy the above, the lens 13 is disposed such that the retina conjugated point of the real light beam coincides with the front focal position, and further, in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, in the single path measurement, the diameters of the light beams are different from each other, and the beam diameter of the light beam 15 is set to be rather small as compared with the light beam 24. Specifically, the beam diameter of the light beam 15 is, for example, about 1 mm at the pupil position of the eye, and the beam diameter of the light beam 24 can be about 7 mm (incidentally, in the drawing, the light beam 15 from the beam splitter 45 to the retina 61 is omitted).

Next, the Hartmann plate 22 as the conversion member will be described.

The Hartmann plate 22 included in the first light receiving optical system 20 is a wavefront conversion member for converting a reflected light flux into plural beams. Here, plural micro-Fresnel lenses disposed on a plane orthogonal to the optical axis apply in the Hartmann plate 22. Besides, in general, with respect to the measurement object part (the eye 60 to be measured), in order to measure a sphere of the eye 60 to be measured, third-order astigmatism aberrations, and other higher order aberrations, it is necessary to perform the measurement with at least 17 beams through the eye 60 to be measured.

Besides, the micro-Fresnel lens is an optical element, and includes, for example, a ring with a height pitch for each wavelength, and a blade optimized for emission parallel to a condensing point. The micro-Fresnel lens here is subjected to, for example, 8-level optical path length variation employing a semiconductor fine working technique, and achieves a high condensing efficiency (for example, 98%).

Besides, the reflected light from the retina 61 of the eye 60 to be measured passes through the afocal lens 42 and the collimate lens 21 and is condensed on the first light receiving part 23 through the Hartmann plate 22. Accordingly, the Hartmann plate 22 includes a wavefront conversion member for converting the reflected light flux into at least 17 beams.

Figure 2:
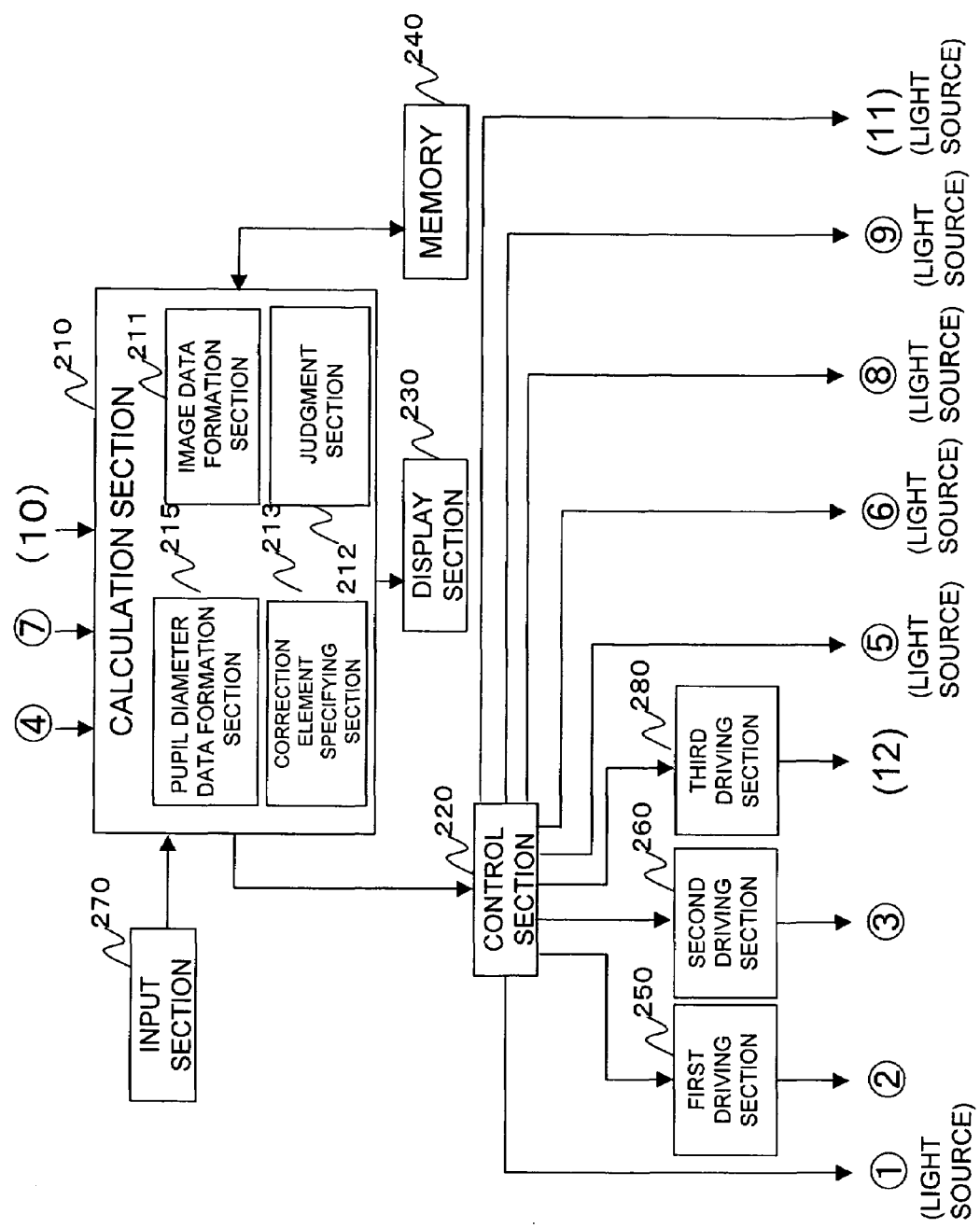
FIG. 2 is a structural view of an electric system 200 of the eye optical characteristic measuring apparatus.

FIG. 2 is a structural view of an electrical system 200 of the eye optical characteristic measuring apparatus. The electrical system 200 of the eye optical characteristic measuring apparatus includes, for example, a calculation section 210, a control section 220, a display section 230, a memory 240, an input section 270, a first driving section 250, a second driving section 260, and a third driving section 280. Besides, the calculation section 210 can include a pupil data formation section 215, an image data formation section 211, a judgment section 212, and a correction element specifying section 123.

The calculation section 210 receives a received light signal (4) obtained from the first light receiving part 23, a received light signal (7) obtained from the second light receiving part 35, and a received light signal (10) obtained from the third light receiving part 54, and performs an arithmetical operation on the origin of coordinates, coordinate axis, movement of coordinates, rotation, pupil diameter, ocular aberrations, corneal wavefront aberrations, Zernike coefficients, aberration coefficients, visual acuity simulation, Strehl ratio (Strehl ratio), phase shift (PTF, phase shift), white light MTF, Landolt's ring pattern, contrast sensitivity and the like. The processing of ideal observed analysis as proposed by Wilson Geiseler may be performed (Geisler, W. S. 1989 Psychological Review 96, pp. 267-324). Besides, signals corresponding to such calculation results are outputted to the control section 220 for performing the whole control of an electric driving system, the display section 230 and the memory 240, respectively. Incidentally, the details of the calculation section 210 will be described later.

The pupil data formation section 215 forms pupil data from an anterior ocular segment image. For example, the pupil data formation section 215 receives the anterior ocular segment image from the second light receiving part 35, calculates points on an edge of a pupil, a focal point, a major axis and a minor axis when the pupil is elliptic, and obtains a pupil diameter. When the pupil area shape is not circular but elliptic or is still another shape, this is specified to obtain measured values used for analysis.

In correction data calculation in after-mentioned template matching or visual acuity simulation, based on the measurement data indicating at least wavefront aberrations of the eye to be examined and in view of a correction element for refraction correction, the image data formation section 211 performs the simulation of visibility of the index for eye examination, and forms index retinal image data. The wavefront aberrations of the eye to be examined include higher order aberrations. That is, parameters of distributions concerning all refractions are included. Based on the index retinal image data formed by the image data formation section 211, the judgment section 212 judges whether or not the index for eye examination is seen.

Besides, the correction element specifying section 213 specifies the correction element to be given to the image data formation section 211. Further, based on the index retinal image data which is corrected with the correction element specified by the correction element specifying section 213 and is formed by the image data formation section 211, the judgment section 212 judges whether or not the appropriate correction element is specified. Besides, the correction element specifying section 213 specifies a correction element based on the result of the judgment section 212, and repeatedly changes the correction element until the judgment section 212 judges that it is the appropriate correction element. The correction element is one of or a combination of two or more of a spherical power, an astigmatic power, and an astigmatic axis angle.

The control part 220 controls lighting and extinction of the first light source part 11 on the basis of the control signal from the arithmetic part 210, or controls the first driving part 250 and the second driving part 260. For example, on the basis of the signals corresponding to the operation results in the arithmetic part 210, the control part outputs a signal (1) to the first light source part 11, outputs a signal (5) to the Placido's disk 71, outputs a signal (6) to the second light source part 31, outputs a signal (8) to the third light source part 51, outputs a signal (9) to the fourth light source part 55, outputs a signal (11) to the fifth light source part 91, and outputs signals to the first driving part 250 and the second driving part 260.

The first driving part 250 is for moving the whole first illuminating optical system 10 in the optical axis direction on the basis of, for example, the received light signal (4) inputted to the arithmetic part 210 from the first light receiving part 23, and outputs a signal (2) to a not-shown suitable lens movement means and drives the lens movement means. By this, the first driving part 250 can perform the movement and adjustment of the first illuminating optical system 10.

The second driving part 260 is for moving the whole first light receiving optical system 20 in the optical axis direction on the basis of, for example, the received light signal (4) inputted to the arithmetic part 210 from the first light receiving part 23, and outputs a signal (3) to a not-shown suitable lens movement means, and drives the lens movement means. By this, the second driving part 260 can perform the movement and adjustment of the first light receiving optical system 20.

The third driving section 280 is for moving a fixation index 92 of the third illuminating optical system 90, and outputs a signal (12) to a not-shown appropriate movement means and drives the movement means. By this, the third driving section 280 can perform the movement and adjustment of the fixation index 92 of the third illuminating optical system 90.

2. Zernike Analysis

Next, a Zernike analysis will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 23 through the Hartmann plate 22.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y) \quad (1)$$

Where, (X, Y) denotes vertical and horizontal coordinates of the Hartmann plate 22.

Besides, with respect to the wavefront aberrations W(X, Y), when the horizontal and vertical coordinates of the first light receiving part 23 are denoted by (x, y), a distance between the Hartmann plate 22 and the first light receiving part 23 is denoted by f, and a movement distance of a point image received by the first light receiving part 23 is denoted by ($\Delta x$, $\Delta y$), the following expression is established.

$$\frac{\partial W(X, Y)}{\partial X} = \frac{\Delta x}{f} \quad (2)$$

$$\frac{\partial W(X, Y)}{\partial Y} = \frac{\Delta y}{f} \quad (3)$$

Where, the Zernike polynomials $Z_i^{2j-i}$ are expressed by the following numerical expressions (4) and (5). (More specifically expressions, for example, see JP-A-2002-209854.)

$$Z_n^m = R_n^m(r) \left\{ \begin{array}{c} \sin \\ \cos \end{array} \right\} \{m\theta\} \quad (4)$$

$m > 0$ sin $m \leq 0$ cos $$R_n^m(r) = \sum_{S=0}^{(n-m)/2} (-1)^S \frac{(n-S)!}{S!\left\{\frac{1}{2}(n-m)-S\right\}!\left\{\frac{1}{2}(n+m)-S\right\}!} r^m \quad (5)$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right] \quad (6)$$

Where, W(X, Y): wavefront aberrations, (X, Y): Hartmann plate coordinates, ($\Delta x$, $\Delta y$): a movement distance of a point image received by the first light receiving part 23, f: a distance between the Hartmann plate 22 and the first light receiving part 23.

The arithmetic part 210 calculates the Zernike coefficients $C_i^{2j-i}$, and uses this to obtain eye optical characteristics such as spherical aberrations, coma aberrations, and astigmatism aberrations.

(Normalization of Pupil Diameter)

A Zernike polynomial always indicates a shape in a circle with a radius of 1, and when Zernike analysis is performed at a certain pupil diameter (pupil diameter), normalization is performed with the pupil radius. For example, when the center coordinate of the pupil with the pupil radius $r_p$ is made (0, 0), a point P(X, Y) in the pupil is made P(X/$r_p$, Y/$r_p$) when the Zernike analysis is performed. When the barycentric point of a spot of a Hartmann image is P, a reference lattice point $P_{ref}$ ($X_{ref}$, $Y_{ref}$) corresponding to this point is made $P_{ref}$($X_{ref}/r_p$, $Y_{ref}/r_p$), and a movement distance of a point image is obtained, and the Zernike coefficients are calculated. The actual wavefront (wavefront in which the coordinates are not normalized) W(X, Y) is expressed by a following expression.

$$W(X, Y) = \sum_{i=0}^{n} \sum_{j=0}^{i} c_i^{2j-i} Z_i^{2j-i}(X/r_p, Y/r_p) \quad (7)$$

$$= \sum_{i=0}^{n} \sum_{j=0}^{i} c_i^{2j-i} Z_i^{2j-i}(x_s, y_s)$$

Where, (X, Y): coordinates not normalized, ($x_s$, $y_s$): coordinates normalized.

3. Landolt's Ring

FIG. 3 is an explanatory view of a Landolt's ring.

Hereinafter, preparation of data of a luminous distribution function Land(x, y) of the Landolt's ring will be described. FIG. 3 shows Landolt's ring of high contrast in upper stand, and Landolt's ring of low contrast in lower stand.

The Landolt's ring is expressed by the reciprocal of a recognizable minimum visual angle, and the ability to be capable of recognizing a visual angle of one minute is called visual acuity of 20/20. For example, if the recognizable minimum visual angle is 2 minutes, the visual acuity is defined as 20/40, and if 10 minutes, the visual acuity is defined as 20/200. In general, the Landolt's ring uses, as an index, a ring in which a gap being ⅕ of the size of the outside ring is provided as shown in the drawing.

When the visual acuity is V, the size d of the Landolt's ring projected on the retina is calculated by $$d = 5 \times 2 \cdot R \tan\left(\frac{1}{60 \cdot V} \times \frac{1}{2}\right) \quad (8)$$

(R: a distance between a pupil and an image point (retina))

On the basis of this expression and the definition of the Landolt's ring, a black portion of the Landolt's ring is made 0 (or 1), a white portion thereof is made 1 (or 0), and the luminous distribution function Land(x, y) of the Landolt's ring is prepared. The data of the prepared luminous distribution function Land(x, y) is stored in the memory 240, is read out by the arithmetic part 210, and is set correspondingly to predetermined visual acuity.

A high contrast original image is such that for example, the contrast of the black portion and the white portion of a Landolt's ring is 100% (for example, the white is 0 and the black is 1), or the figure portion of a Landolt's ring is black (10 cd/m² or less) and the background is white (100 cd/m²) and the actual contrast is 90% or more. Here, the contrast is such that Michelson contrast (I white−I black)/(I white+I black) is expressed by %. On the other hand, as a low contrast original image, one in which the contrast of the black portion and the white portion of a Landolt's ring is 10% (for example, the white is 0 and the black is 0.1) can be used. These contrasts have an accuracy of approximately ±1%. Incidentally, in addition to this example, an appropriate contrast original image may be used. As a luminance distribution function Land (x, y) stored in the memory 240, a high contrast one and a low contrast one are respectively formed and are stored.

4. Ophthalmic Data Measuring Method

Figure 4:
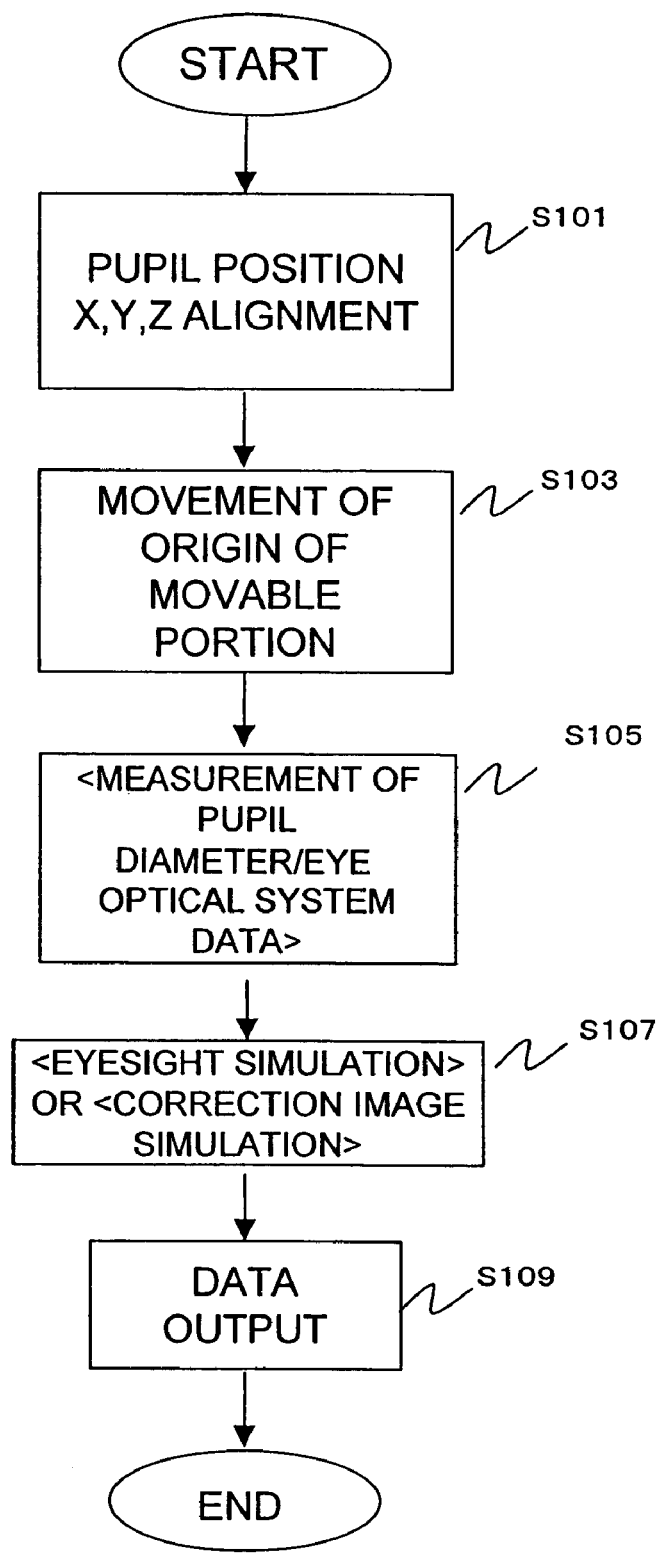
FIG. 4 is flowchart of ophthalmic data measurement.

FIG. 4 is a flowchart of ophthalmic data measurement.

First, the eye optical characteristic measuring apparatus makes alignment of X, Y and Z axes of the pupil position of the eye 60 to be measured (S101). Next, the measuring apparatus moves the origin of a movable section (S103). For example, the Hartmann plate 22, the Placido's disk 71 or the like is set to zero diopter. The calculation section 210 measures the data of the eye optical system, such as the pupil diameter, ocular aberrations and Zernike coefficients, on the basis of the measured received light signals (4), (7) and/or (10) (S105). The calculation section 210 performs a visual acuity simulation or a correction image simulation (S107).

In the visual acuity simulation, for example, at step S107, the calculation section 210 uses, as an evaluation parameter indicating the quality of visibility by the eye 60 to be examined, a comparison result between a simulation result of visibility of the index for eye examination and a predetermined template and/or an MTF (Modulation Transfer Function) indicating the transfer characteristic of the eye to be examined, and estimates the visual acuity of the eye to be examined or the sensitivity in accordance with the evaluation parameter. Incidentally, as the visual acuity, the index for eye examination is suitably set, so that the high contrast visual acuity and low contrast visual acuity can be estimated. Besides, the calculation section 210 estimates optical characteristics such as the MTF of the eye to be examined and the point spread function (PSF).

Besides, in the correction image simulation, for example, the calculation section 210 obtains appropriate correction data while using one of or two or more of the Strehl ratio, the PTF, and the MTF (Modulation Transfer Function) as the evaluation parameter indicating the quality of visibility by the eye 60 to be measured. Besides, the calculation section 210 may obtain appropriate correction data by, for example, performing the simulation of visibility of the index for eye examination and using the comparison result to a predetermined template as an evaluation parameter.

Incidentally, the details of step S105 and S107 will be described later. The calculation section 210 outputs data to the display section 230 and the memory 240 (S109). Incidentally, in the case where data output has already been made in the former processing, the processing of step S109 may be omitted.

Figure 5:
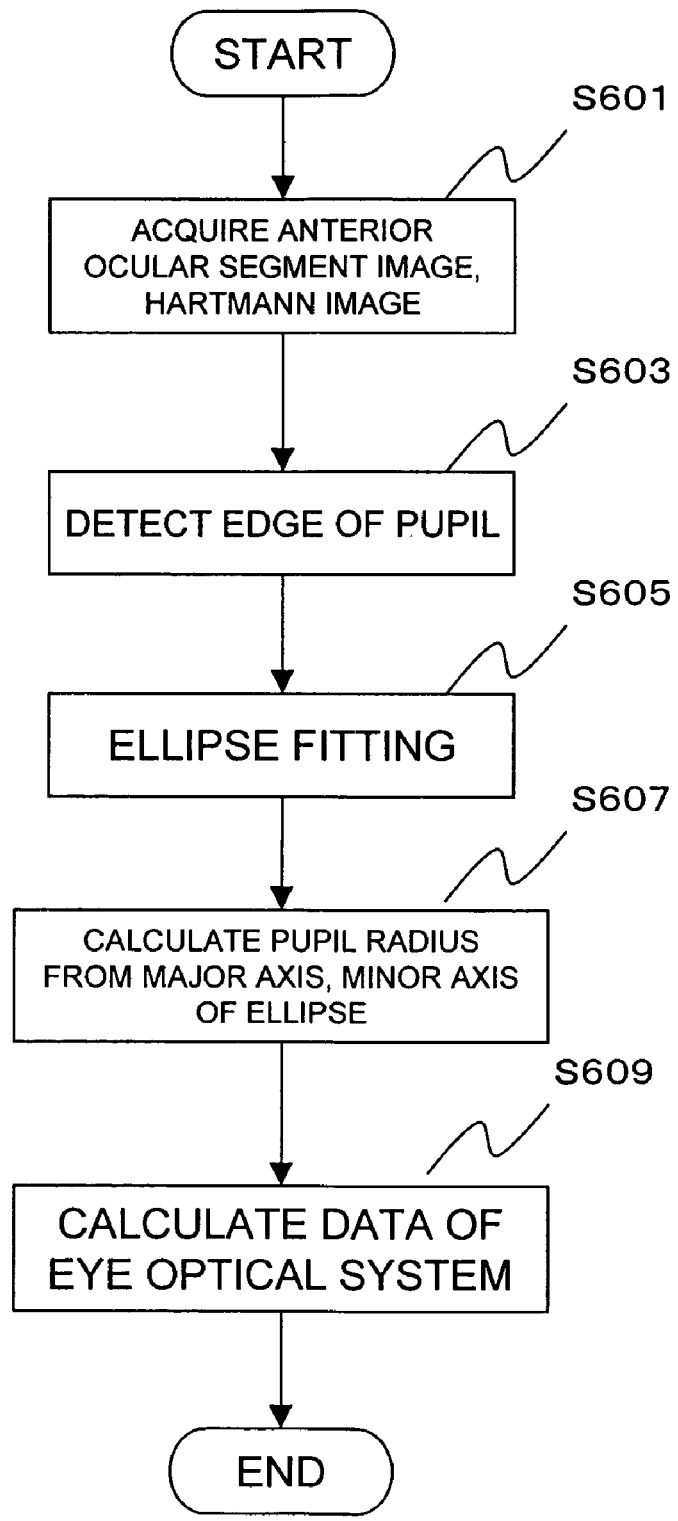
FIG. 5 is a sub-flowchart concerning calculation of a pupil diameter and measurement of eye optical system data.
Figure 6:
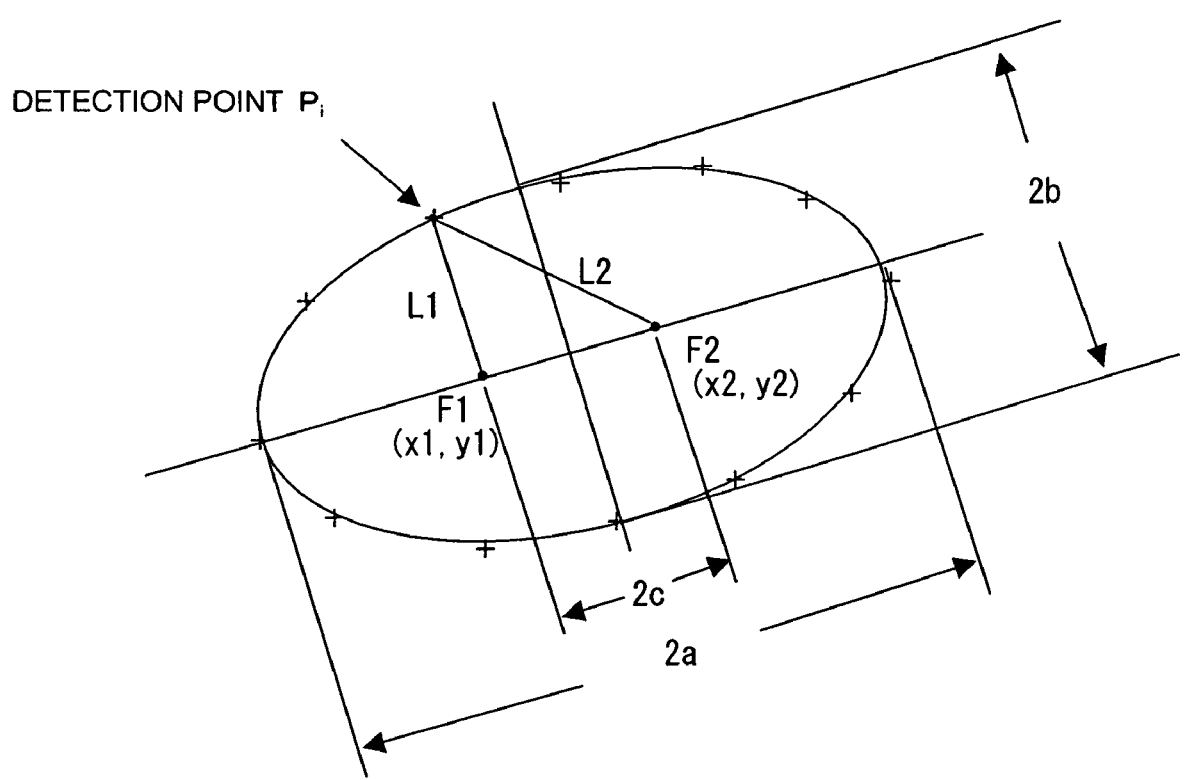
FIG. 6 is an explanatory view of pupil diameter calculation.

FIG. 5 is a sub-flowchart concerning calculation of the pupil diameter at step S105 and measurement of data of the eye optical system. Besides, FIG. 6 is an explanatory view of pupil diameter calculation.

First, the calculation section 210 acquires a Hartmann image and an anterior ocular segment image from the first light receiving part 20 and the second light receiving part 35 (S601). The calculation section 210 causes the fifth light source part 91 to illuminate the eye 60 to be measured in an illumination state of a desired environmental condition (observation condition), and acquires the Hartmann image and the anterior ocular segment image from the first light receiving part 20 and the second light receiving part 35. For example, the calculation section 210 causes the display section 230 to display instructions to select an environmental condition under which the visual acuity or sensitivity is estimated, and the selected environmental condition may be inputted from the input section 270. The environmental condition includes, for example, "seeing in the daytime", "seeing in the twilight" "seeing in a room (under a fluorescent lamp)", "seeing in the nighttime", "normal visual acuity measurement" and the like. Next, the calculation section 210 refers to, for example, a table which is previously stored in the memory 240 and in which the environmental conditions and the illumination states correspond to each other, and acquires the illumination state corresponding to the inputted environmental condition. The illumination states under the respective environmental conditions can be made such that for example, the case of "normal visual acuity measurement" is 50 [1×], "seeing in the daytime" is 100000 [1×], and "in a room (fluorescent lamp)" is 2000 [1×]. Incidentally, with respect to these values, an appropriate value corresponding to the environmental condition can be used. As the environment, it is desirable to use a fixation target larger than a normal one. Here, although the eye 60 to be examined is illuminated in the illumination state of the desired environmental condition by the fifth light source part 91, a structure may be made such that the illumination state is formed by using the surrounding illumination of the eye to be examined or the background illumination.

The calculation section 210 outputs a signal (11) corresponding to the acquired illumination state to the fifth light source part 91 through the control section 220, and causes the eye 60 to be measured to be illuminated. Besides, the calculation section 210 sequentially changes the illumination state from a dark one to a bright one, and can acquire the Hartmann images and anterior ocular segment images in the plural illumination states.

Incidentally, the calculation section 210 may omit step S601, and reads Hartmann image data previously measured and stored in the memory 240, and pupil data including one of the anterior ocular segment image, the pupil shape such as points on the pupil edge, and pupil diameter. Besides, for example, the calculation section 210 may acquire the anterior ocular segment image by reading, as the pupil data in an electric carte, photographic data photographed in the past and stored in the memory 240 from the memory.

Next, based on the acquired anterior ocular segment image, the calculation section 210 detects, for example, 36 (n=36) points $P_i$ (i=1 to n) on the edge of the pupil (S603). The calculation section 210 detects the change (light and shade on the image) of the acquired light amount of the anterior ocular segment image by a method of image processing, and can obtain points on the edge of the pupil. In FIG. 6, the detection points $P_i$ are points indicated by marks of "+".

Next, the calculation section 210 performs elliptic fitting which is fittest to the detected points on the edge of the pupil (S605). First, the calculation section 210 obtains the focal points (points F1 and F2 in FIG. 6) of the ellipse. For example, the calculation section 210 reads the coordinates of two points previously set as the initial values of the focal points from the memory 240. Next, the calculation section 210 obtains distances from the detection point $P_i$ to the two read points, and the sum of the distances is made $L_i$. The calculation section 210 obtains the sum $L_i$ of the distances concerning all the detection points Pi, and obtains a mean value A of Li. Further, the calculation section 210 uses a method of the least square approximation or the like to calculate two points where a square error Se of the sum $L_i$ of the distance and the mean value A expressed by a following expression becomes minimum, and consequently, the focal points of the ellipse can be obtained.

$$S_e = \sum_{i=1}^{n}(L_i - A)^2 \qquad (9)$$

Where, Li: the sum of distances from the point $P_i$ on the edge to the two points F1 and F2, A: the mean value of $L_i$ at the respective points on the edge, n: the number of detected points on the edge. Incidentally, the focal points of the ellipse may be obtained by an appropriate method other than this.

Next, the calculation section 210 obtains the sum L of distances from one point on the ellipse to the focal points. Incidentally, the calculation section 210 may make the foregoing mean value A the sum L of the distances from one point on the ellipse to the focal points. Next, the calculation section 210 calculates the pupil diameter from the length (major axis) of the long axis of the ellipse and the length (minor axis) of the short axis (S607). The length 2a of the long axis and the length 2b of the short axis can be expressed by following expressions.

$$2a = L \qquad (10)$$

$$2b = 2\sqrt{\left(\frac{L}{2}\right)^2 - c^2}$$
$$= 2\sqrt{\frac{L^2}{4} - \frac{(x2-x1)^2 + (y2-y1)^2}{4}}$$
$$= \sqrt{L^2 - (x2-x1)^2 - (y2-y1)^2}$$

Where, L: the sum of distances from a point on the edge to the focal points, (x1, y1), (x2, y2): the focal points of the ellipse. When it is assumed that the pupil diameter $d_p$ is, for example, the mean value of the length 2a of the long axis and the length 2b of the short axis, it is expressed by a following expression.

$$d_p = a + b \qquad (11)$$
$$= \frac{1}{2}\left(L + \sqrt{L^2 - (x2-x1)^2 - (y2-y1)^2}\right)$$

Incidentally, instead of making the mean value the pupil diameter, an appropriate value based on the length 2a of the long axis and the length 2b of the short axis, such as the length of the short axis, the length of the long axis, or an intermediate value of the lengths of the short axis and the long axis, may be used.

The calculation section 210 obtains the pupil center position based on, for example, the focal points of the ellipse and/or the lengths of the long axis and the short axis, and further obtains or specifies the limbus center, and may calculate the shift amount of the pupil center position such as the shift amount from the limbus center. Besides, the calculation section 210 makes the calculated shift amount correspond to the pupil diameter and stores it into the memory 240.

Incidentally, the calculation section 210 may adjust the brightness of the fifth light source part 91 to produce the illumination state in which the pupil diameter in the environment desired by the subjective eye (for example, in an office, in a classroom, driving in the night, etc.) is obtained, in addition to the illumination state in which the pupil diameter in the daytime is obtained. Besides, pupil diameters in the above environments are previously measured and may be used to perform the analysis. By this, the optimum prescription value in the environment desired by the subjective eye can be analyzed. Incidentally, the calculation section 210 may read the measured data and the pupil diameter previously stored in the memory 240 instead of the processing of steps S601 to S607.

The calculation section 210 calculates eye optical system data based on the pupil diameter and the Hartmann image (S609). First, the calculation section 210 detects barycenter points of the respective spots from the Hartmann image acquired at step S601. Next, the calculation section 210 normalizes the barycenter point coordinates detected when the pupil center is made the origin by the pupil radius $r_p$. Here, the pupil radius $r_p$=pupil diameter $d_p/2$. That is, the calculation section 210 sets the barycenter point $P_s(X, Y)$ in the range of the pupil diameter to $P_s(X/r_p, Y/r_p)$, and when the barycenter point of the spot of the Hartmann image is $P_s$, the reference lattice point $P_{ref}(X_{ref}, Y_{ref})$ corresponding to this point is made $P_{ref}(x_{ref}/r_p, y_{ref}/r_p)$. The actual wavefront (wavefront in which the coordinates are not normalized) W(X, Y) is expressed by a following expression.

$$W(X, Y) = \sum_{i=0}^{n}\sum_{j=0}^{i} c_i^{2j-1} Z_i^{2j-1}(X/r_p, Y/r_p) \qquad (12)$$
$$= \sum_{i=0}^{n}\sum_{j=0}^{i} c_i^{2j-1} Z_i^{2j-1}(x_s, y_s)$$

Where, (X, Y): coordinates not normalized, $(x_s, y_s)$: coordinates normalized.

The calculation section 210 uses the normalized coordinates, and calculates the eye optical system data such as the Zernike coefficients and ocular aberrations. Besides, the calculation section 210 stores data into the memory 240 at an appropriate timing.

Figure 7:
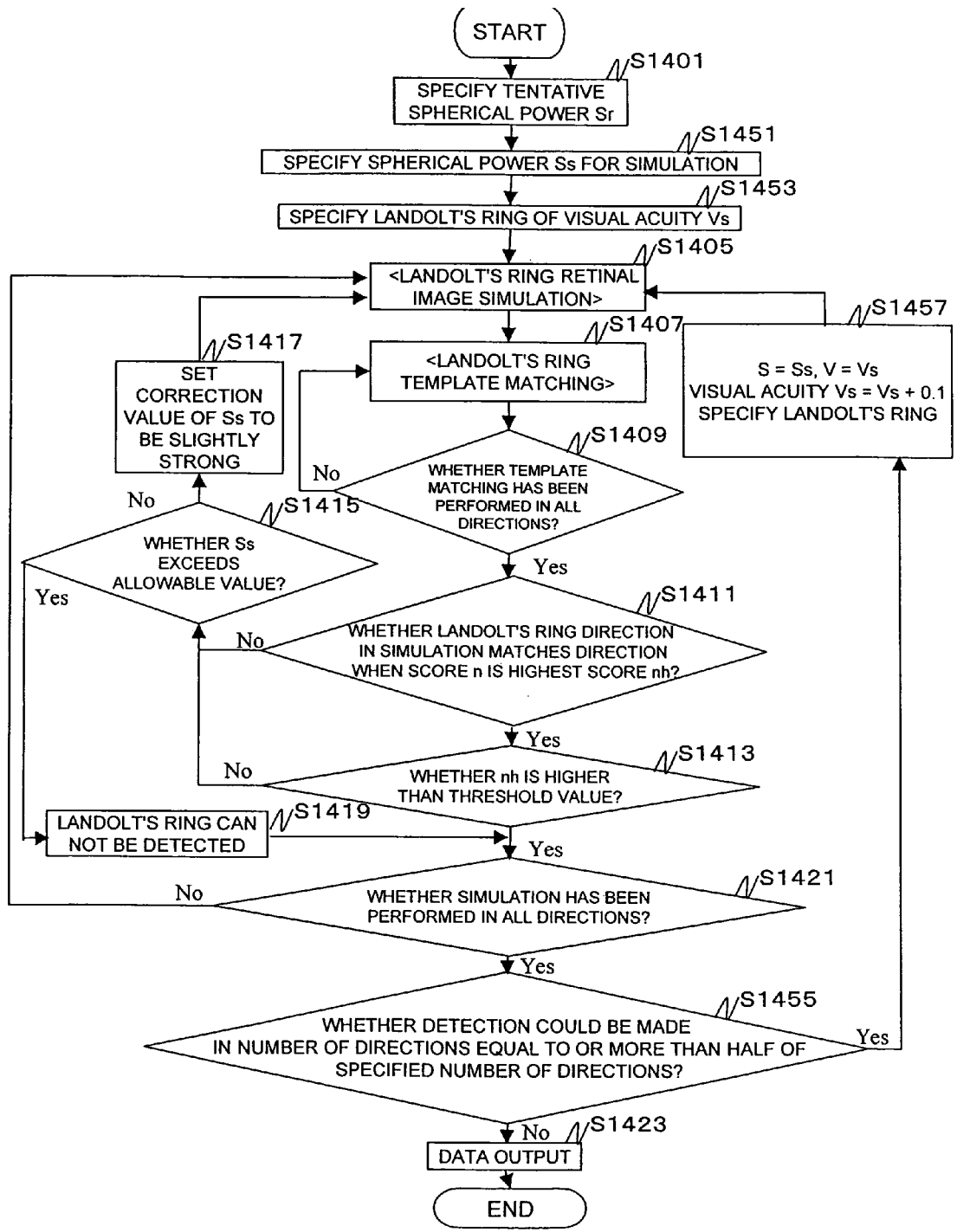
FIG. 7 is a first flowchart of simulation of visual acuity.

5. Visual Acuity Simulation 5-1. First Flowchart (Spherical Power Correction) of Visual Acuity Simulation FIG. 7 shows a first flowchart of visual acuity simulation. FIG. 7 shows the flowchart in which retinal image simulation is performed, a correction spherical power is obtained so that a Landolt's ring can be detected, and the visual acuity at the time of the correction is estimated. Incidentally, in the following respective flowcharts, at steps denoted by the same reference characters, the same processing is performed.

First, the calculation section 210 calculates a tentative spherical power Sr (S1401). As the tentative spherical power Sr, for example, a refractive value or a value calculated from wavefront aberrations may be used, or a value previously stored in the memory 240 or a value inputted from the input section 270 may be used.

Next, the calculation section 210 specifies a spherical power Ss for simulation (S1451). Normally, Ss is specified to be a weak correction with respect to Sr (for example, Ss=Sr+5D). The calculation section 210 specifies the Landolt's ring of a previously determined visual acuity Vs (for example, Vs=0.1) (S1453). At this time, first, the calculation section 210 specifies which of high contrast visual acuity and low contrast visual acuity is estimated. For example, the calculation section 210 may specify the high contrast or low contrast in accordance with the input from the input section 270 or the specification previously stored in the memory 240. In accordance with the specification, the calculation section 210 specifies the Landolt's ring of the high contrast or low contrast corresponding to the previously determined visual acuity Vs.

The image data formation section 211 of the calculation section 210 performs the simulation of a Landolt's ring retinal image to obtain index image data (S1405). Here, the image data formation section 211 performs it with respect to the Landolt's ring in a previously determined direction (for example, a gap of the ring is provided in an upper, lower, right or left direction). That is, in accordance with the wavefront aberrations measured at step S105, the image data formation section 211 obtains index image data indicating the visibility of the Landolt's ring by simulation. The specific processing of this simulation will be described later.

Next, the judgment section 212 of the calculation section 210 performs Landolt's ring template matching (S1407). The judgment section 212 performs the template matching between the index image data obtained by the simulation and the Landolt's ring in a certain direction, and stores the direction at that time and the score n indicating a coincidence degree into the memory 240. The specific processing thereof will be described later.

The judgment section 212 judges whether the template matching is performed in all directions (S1409). Here, in the case of No, advance is made to step S1407, and the processing is repeated until the template matching is performed in all the directions. On the other hand, in the case of Yes at step S1409, the judgment section 212 judges whether the highest score nh of the score n matches the direction of the Landolt's ring of the index image data simulated at step S1405 (S1411). Here, in the case of Yes, the judgment section 212 judges whether the score nh is higher than a previously determined threshold value in the memory 240 or the like (S1413). Incidentally, as the threshold value (threshold value by which a judgment is made as to whether the Landolt's ring can be discriminated), for example, a value obtained by comparison with subjective values of many normal eyes in the past can be used.

In the case of No at step S1411 or S1413, the judgment section 212 judges whether Ss exceeds a previously determined allowable value (for example, Sr-5D) (S1415). Here, in the case of No, the correction element specifying section 213 sets the correction element of Ss to be slightly strong (for example, Ss-0.25D) (S1417), and the image data formation section 211 performs the simulation of the Landolt's ring retinal image based on this correction element. The calculation section 210 performs the processing subsequent to step S1407 concerning the index image data obtained by this simulation. On the other hand, in the case of Yes at step S1415, the judgment section 212 judges that the Landolt's ring can not be detected (S1419), and stores the direction at this time and that the detection could not be made in this direction into the memory 240.

After step S1419 or in the case of Yes at step S1413, the judgment section 212 judges whether simulation has been performed in all directions of the Landolt's ring (S1421). Here, in the case of No, return is made to step S1405, and the calculation section 210 repeats the foregoing processing in all directions. On the other hand, in the case of Yes at step S1421, the judgment section 212 judges whether detection could be made in number equal to or more than half of specified number of directions (S1455).

In the case of Yes at step S1455, the correction element specifying section 213 specifies S=Ss and V=Vs, and specifies the Landolt's ring of visual acuity Vs=Vs+0.1 (S1457). At this time, as the specified Landolt's ring, in accordance with the specification at step S1453, the Landolt's ring of the high contrast or low contrast is specified. Thereafter, advance is made to step S1405, the image data formation section 211 performs the simulation of the retinal image based on the specified correction element and Landolt's ring to obtain index image data, and performs the processing subsequent to step S1407. On the other hand, in the case of No at step S1455, the calculation section 210 performs data output (S1423). That is, the calculation section 210 displays the visual acuity V at this time, the spherical power S=Ss, the direction of the Landolt's ring which could be detected, simulation result and the like on the display section 230 and stores them into the memory 240. Incidentally, the calculation section 210 may use decimal visual acuity as the visual acuity, or may use logMAR (log Minimum Angle Resolution) visual acuity. The logMAR visual acuity is the visual acuity expressed by the logarithm of minimum vision. Incidentally, the data to be displayed and stored are not limited to the foregoing, and appropriate data can be displayed and stored. Besides, it may be suitably selected among the foregoing data. For example, data except the visual acuity V may be displayed.

Figure 8:
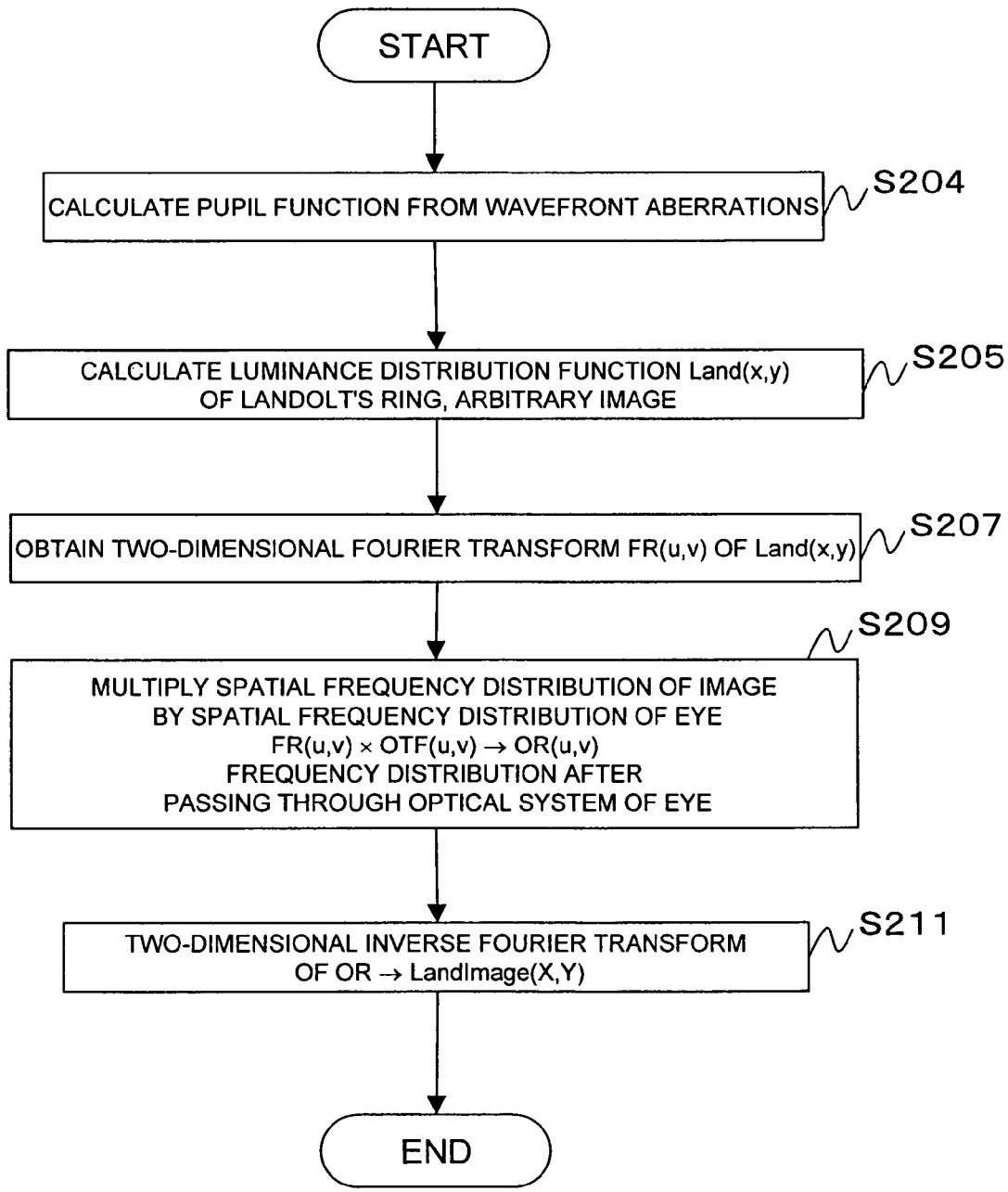
FIG. 8 is a flowchart of simulation of a retinal image.

FIG. 8 is a flowchart of the simulation of a retinal image at the above step S1405. First, the calculation section 210 calculates a pupil function f(x, y) based on the wavefront aberration W(X, Y) obtained at step S105 of FIG. 4 and the specified correction element by a following expression (S204).

$$f(x,y)=e^{ikW(X,Y)} \tag{13}$$

The calculation section 210 refers to the memory 240 and calculates the luminance distribution function Land(x, y) of the Landolt's ring (or an arbitrary image) (S205). The calculation section 210 performs the two-dimensional Fourier transform of Land(x, y) to obtain a spatial frequency distribution FR(u, v) (S207). The calculation section 210 calculates a spatial frequency distribution OTF of the eye based on the pupil function, and obtains a frequency distribution OR(u, v) after passing through the eye optical system by multiplying the spatial frequency distribution FR(u, v) of the Landolt's ring (or arbitrary image) by the spatial frequency distribution OTF(u, v) of the eye (S209) as follows.

$$FR(u, v) \times OTF(u, v) \rightarrow OR(u, v)$$

Incidentally, the specific calculation method of the OTF will be described later.

Next, the calculation section 210 performs the two-dimensional inverse Fourier transform of OR(u, v) to obtain the luminance distribution image LandImage (X, Y) of the Landolt's ring (or arbitrary image) (S211).

FIG. 9 is an explanatory view of template matching of step S1407. As shown in the drawing, a template image (lower drawing) is specified correspondingly to the Landolt's ring original image (upper drawing), and the template image as stated above is stored in the memory 240 correspondingly to an identifier indicating the size of the Landolt's ring. Although the template image is such that in this example, b is made b=1.5a, the number of pixels of the Landolt's ring is N1, the pixel number is 1, the number of pixels of a blurred point image part around the Landolt's ring is N2, and the pixel value is −N1/N2, it is not limited to this but can be suitably specified. Besides, although the Landolt's ring original image shown on the upper part of FIG. 9 shows the Landolt's ring original image of high contrast, also in the case where the Landolt's ring original image of low contrast is used, a similar template can be used.

Figure 10:
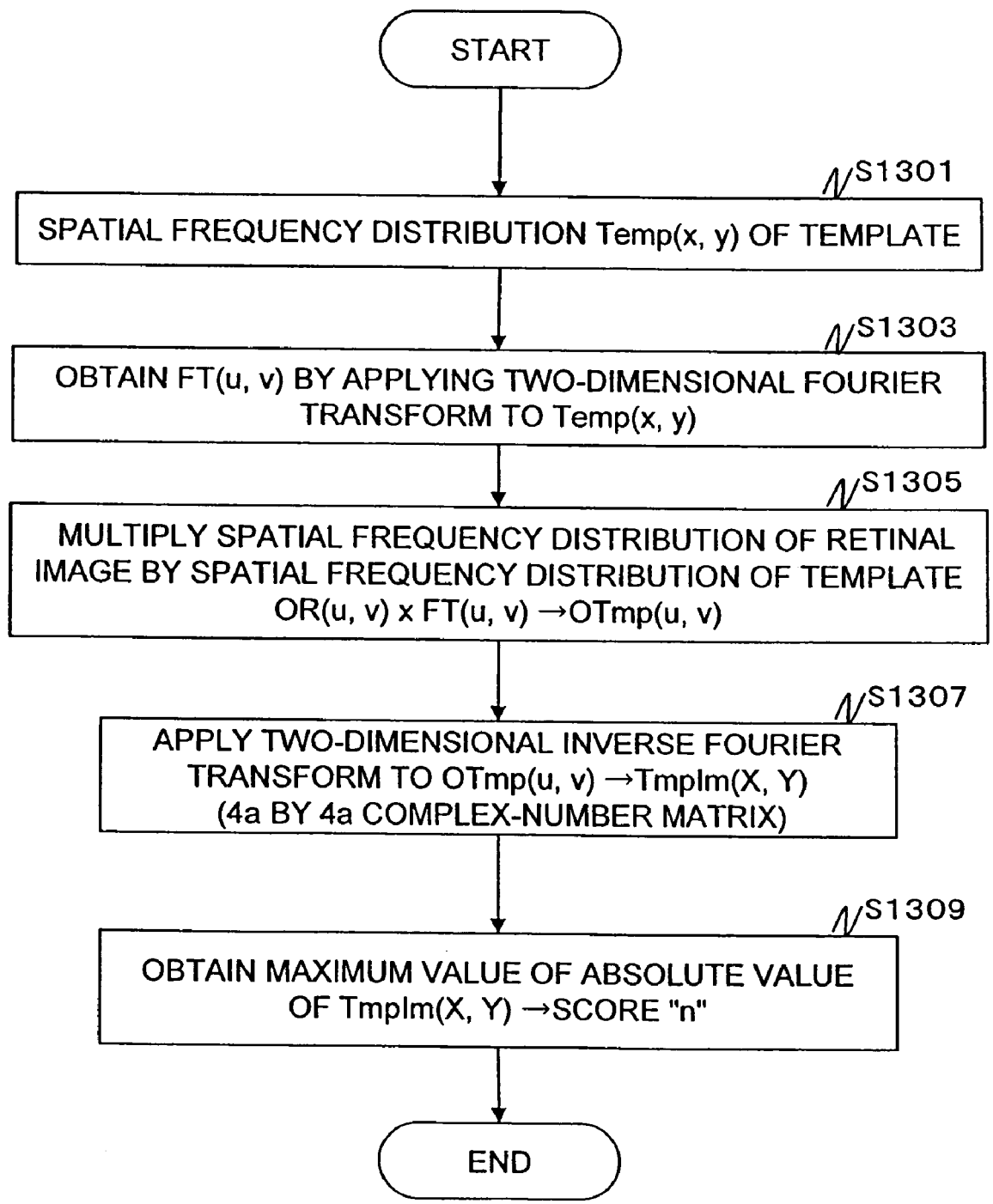
FIG. 10 is a flowchart of Landolt's ring template matching.

FIG. 10 shows a flowchart of the Landolt's ring template matching at step S1407.

The calculation section 210 reads the template image from the memory 240 in accordance with the size of the specified Landolt's ring, and obtains the spatial frequency distribution Temp(x, y) thereof (S1301). Next, the calculation section 210 obtains the two-dimensional Fourier transform FT(u, v) of Temp(x, y) (S1303). The calculation section 210 obtains the two-dimensional Fourier transform OR(u, v) of the spatial frequency distribution of the index image data by the simulation of the retinal image, and multiplies OR(u, v) by the spatial frequency distribution FT(u, v) of the template as indicated by a following expression, and obtains OTmp(u, v) (S1305).

$$OR(u, v) \times FT(u, v) \to OTmp(u, v)$$

The calculation section 210 performs the two-dimensional inverse Fourier transform of OTmp(u, v) to obtain TmpIm(X, Y) (complex matrix of 4a×4a) (S1307). The calculation section 210 acquires the maximum value of the absolute value of TmpIm(X, Y) to obtain the score n (S1309).

By taking such a correlation, when the simulation index image is close to the original image, the score is high, and in the case of blur, the score becomes low according to that.

5-2. Second Flowchart (Astigmatic Correction −1) of Visual Acuity Simulation

Figure 11:
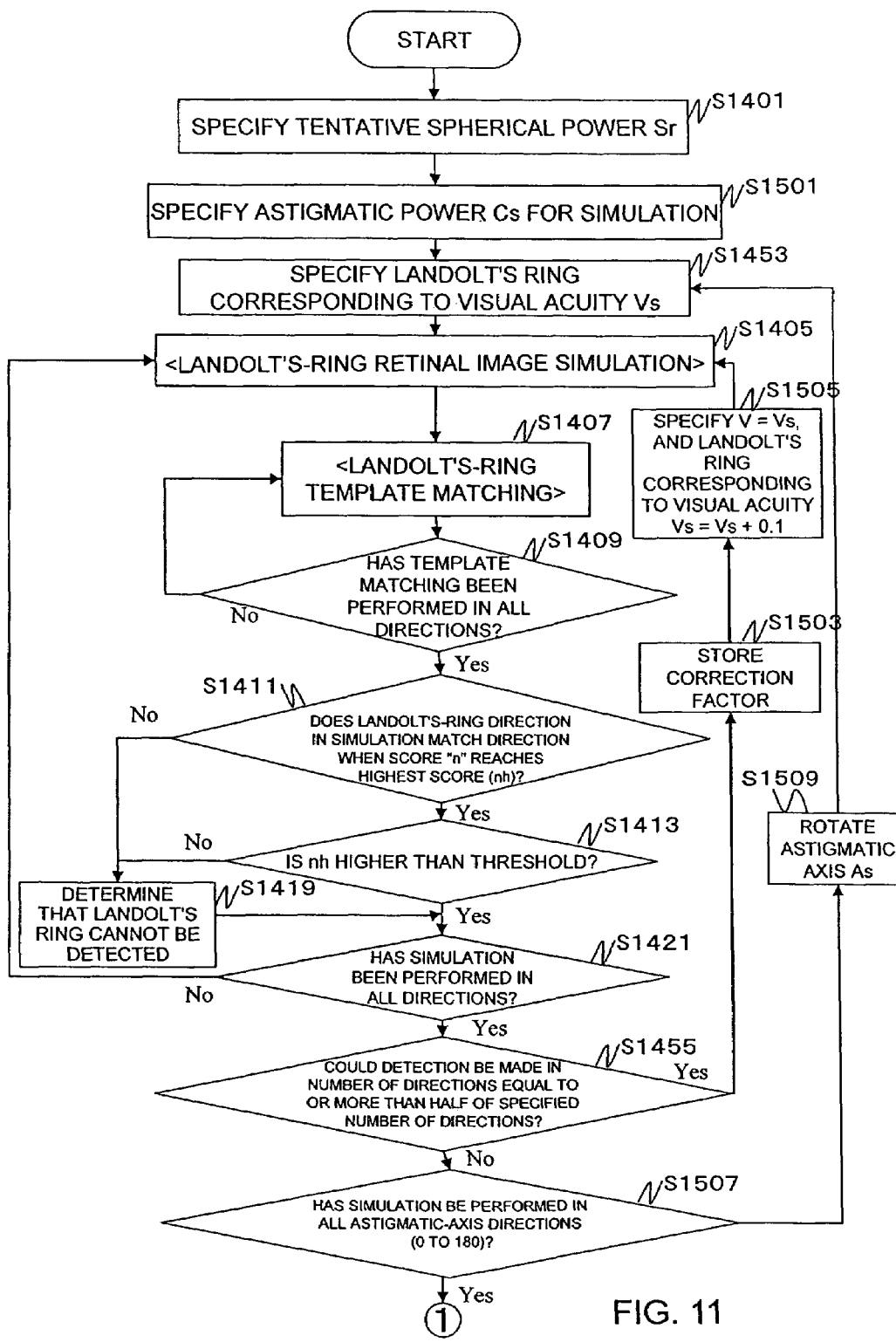
FIG. 11 is a second flowchart (1) of simulation of visual acuity.
Figure 12:
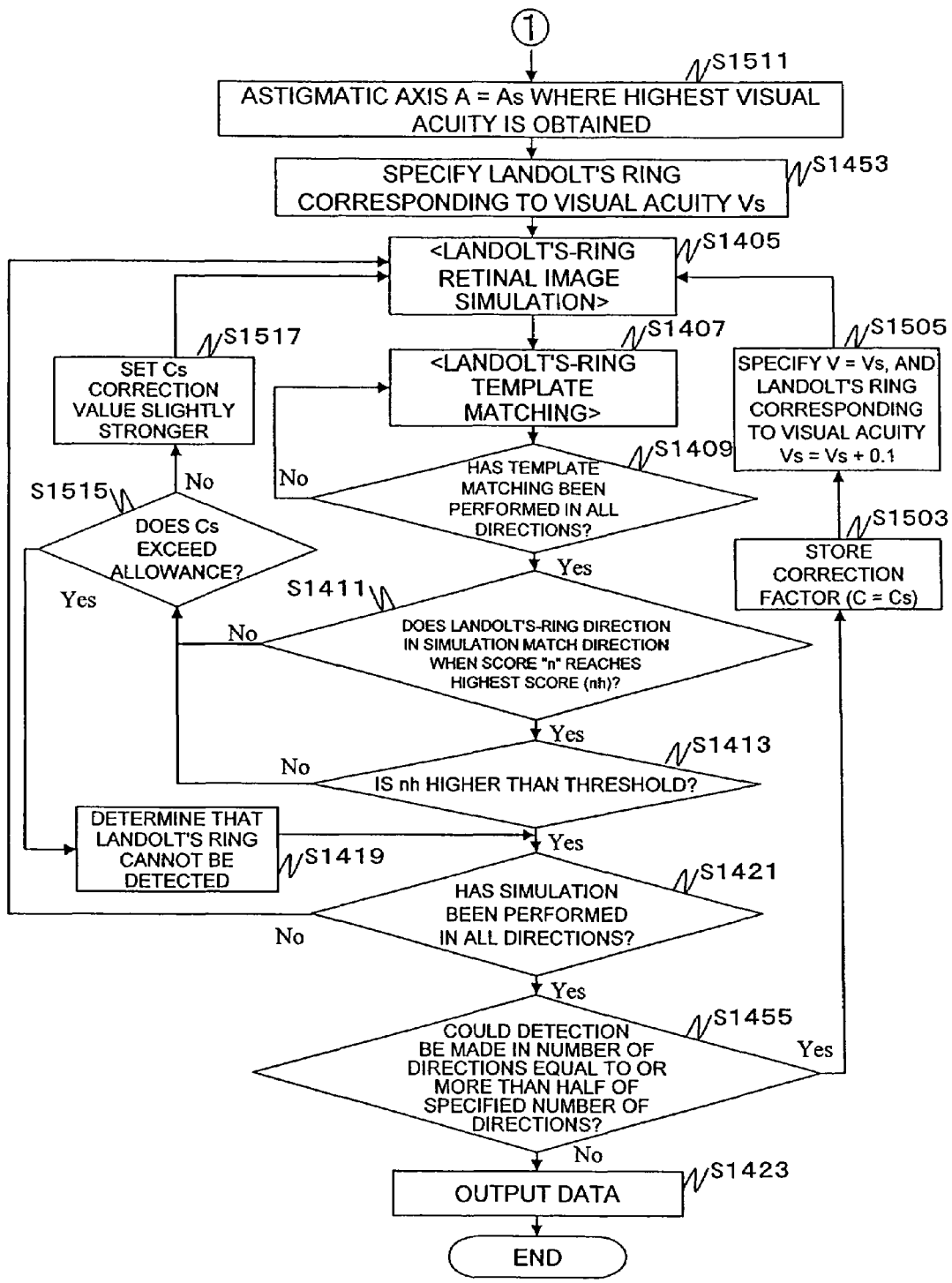
FIG. 12 is a second flowchart (2) of simulation of visual acuity.

FIGS. 11 and 12 show second flowcharts (1) and (2) of the visual acuity simulation. FIGS. 11 and 12 show the flowcharts in which the simulation of a retinal image is performed, a correction astigmatic axis A and an astigmatic power C are obtained so that the Landolt's ring can be detected, and the visual acuity at the time of the correction is estimated. This example shows a case where the astigmatic power has a negative value.

Similarly to step S1401, the calculation section 210 calculates a tentative spherical power Sr (S1401). By specifying the tentative spherical power Sr, in order to avoid the retina from approaching the front focal line relatively to the rear focal line, it may be set to be slightly weaker correction than Sr specified at step S1401 (for example, Sr→Sr+0.5D). Alternatively, what is obtained by subtracting the refractive value or ½ of the astigmatic power Cs calculated from the wavefront aberrations from S obtained as described above, or what is specified to be slightly weaker correction than them may be used. Next, the calculation section 210 specifies the astigmatic power Cs for simulation (S1501). For example, Cs may be obtained by using the refractive value or the astigmatic power C calculated from the wavefront aberrations, or a correspondence table storing Cs corresponding to correction elements such as S or C or Zernike coefficients is stored in the memory 240, and it may be obtained by referring to that. Next, the calculation section 210 specifies the Landolt's ring of visual acuity Vs (for example, Vs=0.1) similarly to the above (S1453).

At steps S1405 to S1413, similarly to the above, the calculation section 210 performs the processing such as the Landolt's ring retinal image simulation and Landolt's ring template matching. In the case of No at step S1411 or S1413, the judgment part 212 judges that the Landolt's ring can not be detected, and stores the direction at this time and that the detection could not be made in this direction into the memory 240 (S1419). After step S1419 or in the case of Yes at step S1413, similarly to the above, the calculation section 210 performs the processing of step S1421 and S1455.

At step S1455, in the case where it is judged that detection could be made in number of directions equal to or more than half of specified number of direction, the calculation section 210 stores the specified correction element into the memory 240 (S1503). Next, the correction element specifying section 213 specifies V=Vs, and specifies the Landolt's ring of visual acuity Vs=Vs+0.1 (S1505). At this time, with respect to the Landolt's ring to be specified, in accordance with the specification at step S1453, the Landolt's ring of high contrast or low contrast is specified. Thereafter, advance is made to S1405, and the image data formation section 211 performs the retinal image simulation based on the specified correction element and the Landolt's ring to obtain index image data, and performs the processing subsequent to step S1407.

On the other hand, in the case of No at step S1455, the judgment section 212 judges whether the simulation is performed in all astigmatic axis angle directions (0 to 180) (S1507). Here, in the case of No, the correction element specifying section 213 rotates the astigmatic axis angle As (for example, As=As+5) (S1509). Thereafter, advance is made to step S1453, and the processing subsequent to step S1453 is repeatedly performed.

Next, referring to FIG. 12, in the case where the judgment section 212 makes a judgment of Yes at step S1507, the correction element specifying section 213 of the calculation section 210 substitutes, as the astigmatic axis angle A, As at the time when the visual acuity V is largest (S1511). Incidentally, when there are plural As at the time when it is largest, one at which the number of Landolt's rings which could be detected by the visual acuity V is largest is specified as the astigmatic axis angle A, and further, when there are plural such As, one is specified at which the sum of nh in the direction in which detection by the visual acuity V could be made becomes maximum. By this, the astigmatic axis angle A is determined.

At steps S1453, and S1405 to S1413, as described in the above embodiment, based on the specified Sr, Cs and A, the calculation section 210 performs the respective processings such as the Landolt's ring retinal image simulation and the Landolt's ring template matching.

In the case of No at step S1411 or S1413, the judgment section 212 judges whether Cs exceeds a previously determined allowable value (for example, Cs-10D) (S1515). Here, in the case of No, the correction element specifying section 213 specifies the correction element of Cs to be slightly strong (for example, Cs-0.25D) (S1517), the image data formation section 211 performs the Landolt's ring retinal image simulation based on this correction element (S1405). The calculation section 210 repeatedly performs the processing subsequent to step S1407 with respect to the index image data obtained by this simulation. On the other hand, in the case of Yes at step S1515, the judgment section 212 judges that the Landolt's ring can not be detected (S1419), and stores the direction at this time and that the detection could not be made in this direction into the memory 240.

After step S1419 or in the case of Yes at step S1413, similarly to the above, the calculation section 210 performs the processing of step S1421 and S1455. In the case of Yes at step S1455, the calculation section 210 performs the processing of step S1503 and S1505. The processing of the respective steps is the same as the above. Thereafter, advance is made to step S1405, and the image data formation section 211 performs the retinal image simulation based on the specified correction element and the Landolt's ring to obtain the index image data, and performs the processing subsequent to step S1407.

On the other hand, in the case of No at step S1455, the calculation section 210 performs the data output (S1423). That is, the calculation section 210 displays the visual acuity V at this time, the astigmatic power C=Cs, the astigmatic axis A, the spherical power S=Sr, the direction in which detection could be made, the simulation result and the like on the display section 230 and stores them in the memory 240.

5-3. Third Flowchart (Astigmatic Correction −2) of Visual Acuity Simulation

Figure 13:
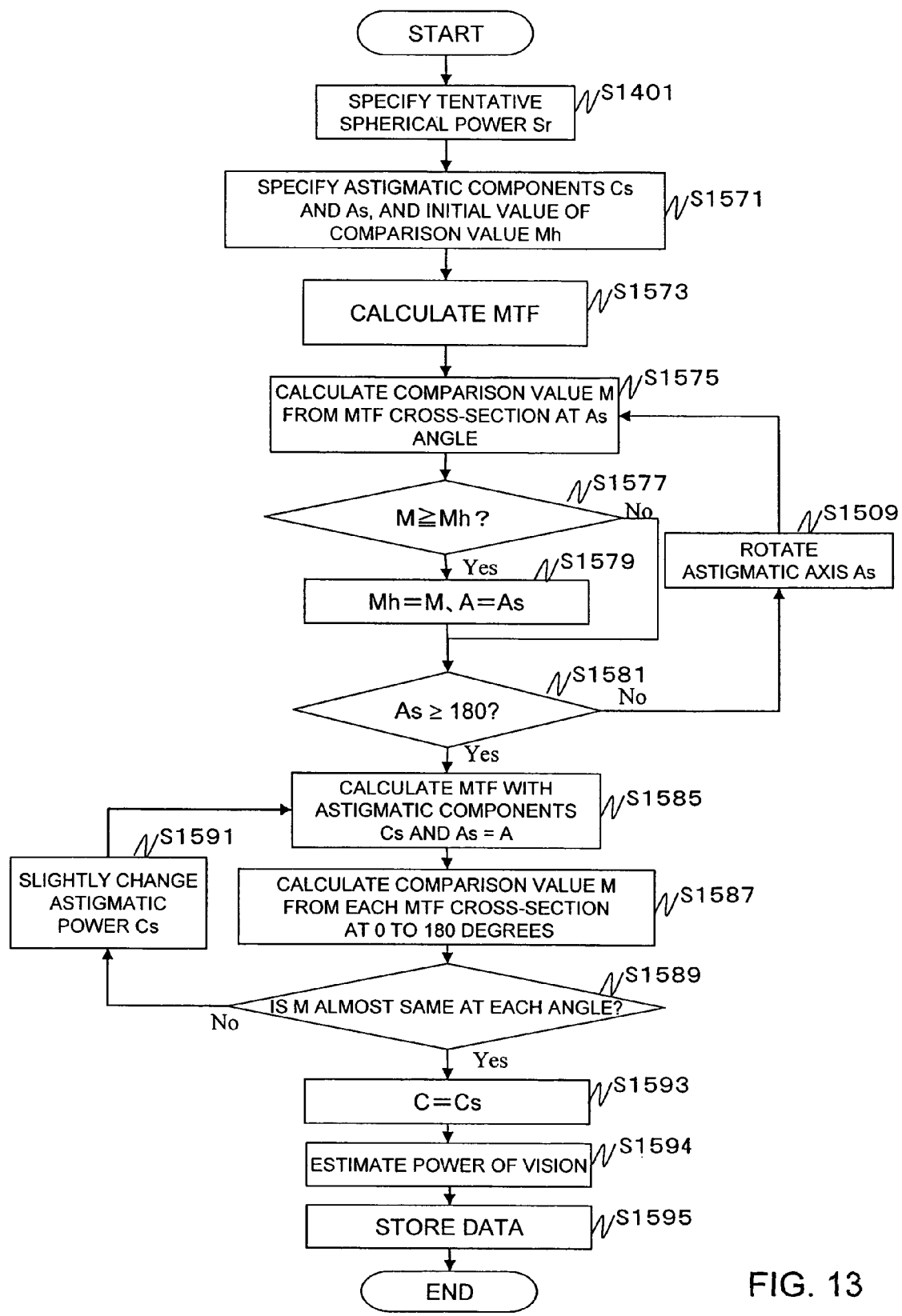
FIG. 13 is a third flowchart of simulation of visual acuity.

FIG. 13 shows a third flowchart of the visual acuity simulation. FIG. 13 shows the flowchart in which the MTF is used as an evaluation parameter to obtain the astigmatic axis A and the astigmatic power C, and the visual acuity at the time of the correction is estimated.

In step S1401, as described above, the arithmetic part 210 calculates a tentative spherical power Sr. Then, the arithmetic part 210 initially specifies an astigmatic power Cs and the angle As of an astigmatic axis, both of which are astigmatic components, and a comparison numeral Mh (S1571). These values may be stored in advance in the memory 240, or may be input through the input part. The arithmetic part 210 initially specifies, for example, Cs=0, As=0, and Mh=0.

The arithmetic part 210 calculates the MTF (modulation transfer function) (S1573) according to the wavefront aberrations obtained before. A specific MTF calculation method will be described later. The arithmetic part 210 calculates a comparison numeral M from an MTF cross-section at the specified angle As of the astigmatic axis (S1575). As the comparison numeral M, the total sum of MTF values, an MTF cross-section, or the sum of 3, 6, 12, and 18 cpd, for example, can be used. The arithmetic part 210 stores currently set As and M in the memory 240.

The determination part 212 of the arithmetic part 210 determines whether M≧Mh (S1577). If no, the processing proceeds to step S1581. If yes, the correction-factor setting part 213 of the arithmetic part 210 sets Mh=M and A=As (S1579). Then, the determination part 212 determines whether As is 180 or larger (S1581). If no, the correction-factor setting part 213 rotates the angle As of the astigmatic axis (for example, As=As+5) (S1509). Then, the arithmetic part 210 goes back to step S1575 and repeats the processes to obtain the maximum value of M in an axis-angle range of 0 to 180 degrees and the angle As (weak main longitude line or strong main longitude line) of the astigmatic axis equal to the direction where the maximum value of M is obtained.

If yes in step S1581, in other words, if the angle A of the astigmatic axis is obtained, the arithmetic part 210 calculates the MTF according to the astigmatic components Cs and As=A. The arithmetic part 210 further calculates the comparison numeral M from each MTF cross-section at 0 to 180 degrees (for example, at an interval of 5 degrees).

The determination part 212 determines whether the calculated Ms are almost equal at the angles (S1589). For example, it can be determined by determining whether the difference between the maximum value of M and the minimum value of M is smaller than a predetermined threshold. If no in step S1589, the arithmetic part 210 slightly changes the astigmatic power Cs (for example, Cs=Cs-0.25) (S1591), and the processes of step S1585 and subsequent steps are repeated. If yes in step S1589, the arithmetic part 210 specifies C=Cs (S1593).

The calculation section 210 estimates the visual acuity after the correction based on the obtained astigmatic power C and the astigmatic axis angle A (S1594). For example, the calculation section 210 performs the processing of a fourth flowchart described later to estimate the visual acuity after the correction. Incidentally, instead of estimating the visual acuity or in addition to the estimation of the visual acuity, the calculation section 210 may obtain the contrast sensitivity.

The calculation section 210 stores the obtained astigmatic power C and the astigmatic axis angle A into the memory 240 and displays them on the display section 230 as the need arises (S1595).

5-4. Visual Acuity Estimation

Figure 14:
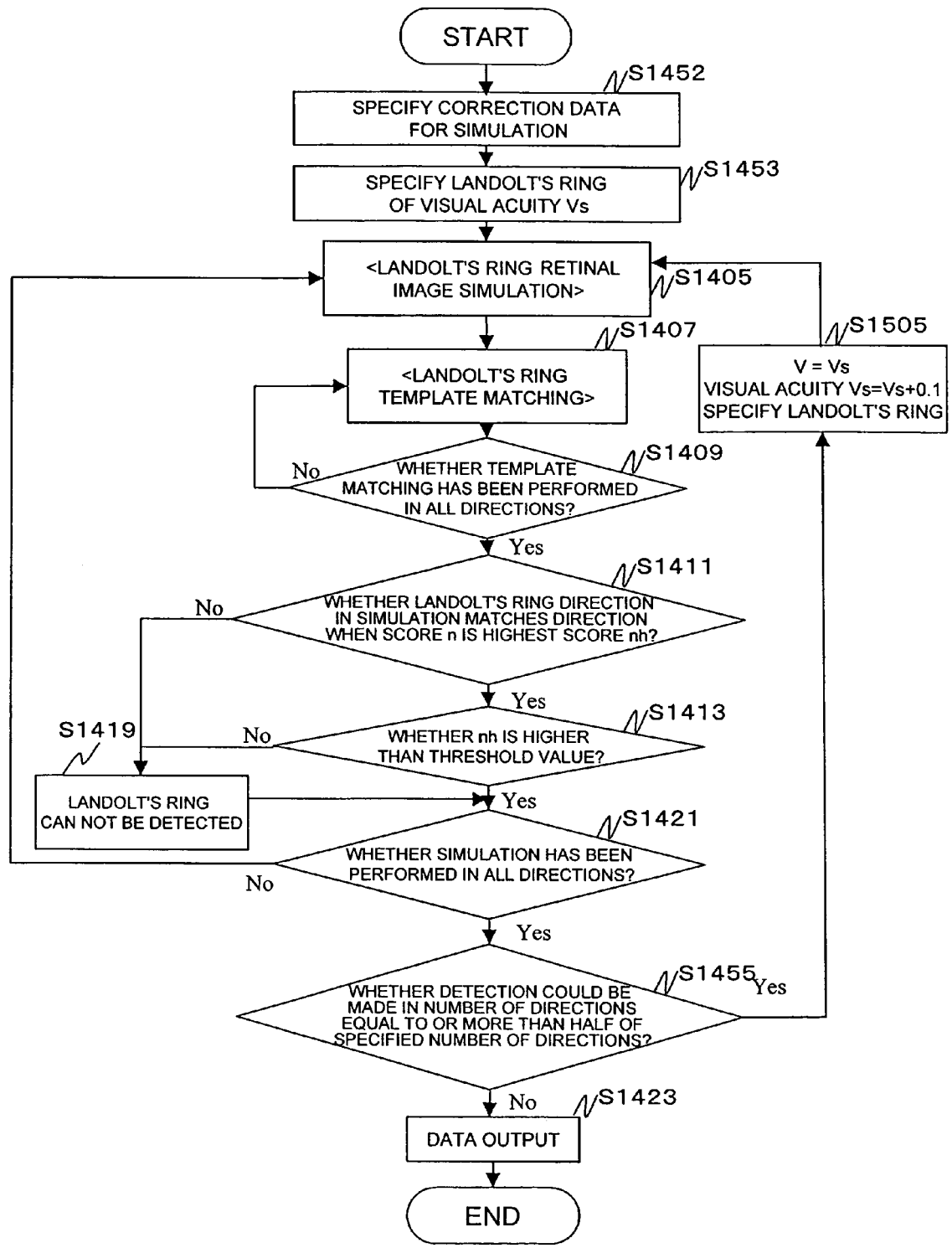
FIG. 14 is a fourth flowchart of simulation of visual acuity.

FIG. 14 is a fourth flowchart of the visual acuity simulation of step S107. Besides, the flowchart shown in FIG. 14 is also a sub-flowchart of the foregoing step S1594. First, the calculation section 210 specifies correction data for simulation (S1452). For example, the calculation section 210 can use, as the correction data, a value calculated based on the refractive value or wavefront aberrations, or the spherical power S obtained as stated above, the astigmatic power C, or the astigmatic axis angle A. Besides, by setting the respective elements of the correction data to be 0, the calculation section 210 can estimate the visual acuity in the environment of the subjective eye when the correction is not made. Besides, for example, the calculation section 210 may specify the astigmatic power C, the astigmatic axis angle A, and/or the spherical power correction S, which are obtained by performing the processing of the foregoing flowchart. Since the processing of each step subsequent to step S1453 is the same as the processing denoted by the same reference character in the flowcharts shown in FIGS. 7 and 11, the detailed description will be omitted.

5-5. Contrast Sensitivity

The calculation section 210 can calculate contrast sensitivity as the visual acuity simulation of step S107. The calculation section 210 obtains Mopt(r, s) of the eye optical system based on the wavefront aberrations, and calculates the contrast sensitivity based on the obtained MTF. Besides, the calculation section 210 displays the calculated contrast sensitivity on the display section 230 or stores it into the memory 240. Incidentally, the contrast sensitivity is not only calculated in the processing of step S107, but also can be calculated during the processing of the first to fourth flowcharts and can be displayed.

(MTF Calculation)

First, the calculation of the MTF (Modulation transfer function) will be described.

The MTF is an index indicating the transfer characteristic of the spatial frequency, and is widely used to express the performance of an optical system. In this MTF, visibility can be predicted by obtaining, for example, the transfer characteristic for 0 to 100 sinusoidal gray lattices per degree. In this embodiment, as described below, a monochromatic MTF may be used or a white MTF may be used.

First, the monochromatic MTF is calculated from the wavefront aberration W(x, y). Incidentally, W(x, y) is an input value (measured value), and with respect to the corneal aberrations, the corneal wavefront aberrations obtained from the cornea shape can also be used.

When the monochromatic MTF is obtained, the calculation section 210 obtains the pupil function f(x, y) from the wavefront aberrations as described below.

$$f(x, y) = e^{ikW(x, y)}$$

(i: imaginary number, k: wave number vector ($2\pi/\lambda$), $\lambda$: wavelength)

At this time, in view of the Stiles-Crawford effect, $(e^{-ar_p})^2$ (a is, for example, approximately 0.05) may be multiplied. Here, $r_p$ is the radius of the pupil.

The calculation section 210 performs the Fourier transform of this pupil function f(x, y) to obtain an amplitude distribution U(u, v) of point images as indicated by a following expression.

$$\text{Amplitude } U(u, v) = \int\int_{-\infty}^{\infty} f(x, y) \exp\left[-\frac{i}{R}\frac{2\pi}{\lambda}(ux+vy)\right] dx dy \quad (14)$$

($\lambda$: wavelength
R: distance from the pupil to an image point (retina)
(u, v): coordinate value in a plane perpendicular to the optical axis while the image point O is made the origin
(x, y): coordinate value in the pupil plane)

The calculation section 210 multiplies U(u, v) by its complex conjugate and obtains I(u, v) as the point spread function (PSF) by a following expression.

$$I(u,v) = U(u, v)U^*(u, v)$$

Next, the calculation section 210 performs the Fourier transform (or autocorrelation) of PSF to perform normalization, and obtains OTF.

$$R(r, s) = \int\int_{-\infty}^{\infty} I(u, v) e^{-i2\pi(ru+sv)} du dv \quad (15)$$

(r, s: variables in spatial frequency area)

$$OTF = \frac{R(r, s)}{R(0, 0)}$$

Besides, since the magnitude of the OTF is the MTF, $$MTF(r, s) = |OTF(u, v)|$$

is established.

The white-color MTF is calculated from the single-color MTF, obtained as described above.

To obtain the white-color MTF, the MTF is weighted at each wavelength and added. Since the above-described MTF has a different value at each wavelength, the MTF can be expressed in the following way when the MTF at a wavelength $\lambda$ is indicated by $MTF_\lambda$.

$$MTF(r, s) = \frac{\int \omega_\lambda MTF_\lambda(r, s) d\lambda}{\int \omega_\lambda d\lambda} \quad (16)$$

The MTF is highly weighted at visible-light wavelengths, and the calculation is made.

More specifically, the MTF is obtained in the following way when it is assumed, for example, that the three primary colors (R, G, and B) are specified such that red light has a wavelength of 656.27 nm with a weight of 1, green light has a wavelength of 587.56 nm with a weight of 2, and blue light has a wavelength of 486.13 nm with a weight of 1.

$$MTF(r, s) = (1 \times MTF_{656.27} + 2 \times MTF_{587.56} + 1 \times MTF_{486.13})/(1+2+1)$$

Since the white-light MTF is measured only at one wavelength (840 nm), calibration may be performed for other wavelengths according to the result of measurement, as compensation, to obtain the MTF at each wavelength. More specifically, when the eye optical characteristic measuring apparatus measures eye aberration, for example, at 840 nm, color aberration $W_A(X, y)$ corresponding to a shift from the wavefront aberrations $W_{840}(x, y)$ at a wavelength of 840 nm is measured with the use of an eye model, $W_{840}(x, y)$ is added to the color aberration $W_A(x, y)$, and the MTF is calculated at each wavelength from this wavefront aberrations in the following way.

$$W_\lambda(x, y) = W_{840}(x, y) + W_A(x, y)$$

(Contrast Sensitivity Calculation)

Next, the contrast sensitivity will be described. The contrast sensitivity is expressed by a following expression (Peter G. J. Barten, "Contrast Sensitivity of the Human Eye and Effects on Image Quality", SPIE Optical Engineering Press 1999).

$$S(r, s) = \frac{M_{opt}(r, s)/k}{\sqrt{\frac{4}{T}\left(\frac{1}{X_o^2} + \frac{1}{X_{\max}^2} + \frac{u^2}{N_{\max}^2}\right)\left(\frac{1}{\eta p E} + \frac{\Phi_0}{1 - e^{-(\sqrt{r^2+s^2}/u_0)^2}}\right)}} \quad (17)$$

Where, the respective parameters are as follows: $M_{opt}(r, s)$: MTF of the eye optical system, k: S/N ratio: 3, T: weighting time of a nervous system: 0.1 sec, $X_o$: visual angle of a matter: 3.8 deg, $X_{max}$: maximum visual angle of space weighting: 12 deg, $N_{max}$: maximum frequency when weighting is performed: 15 cycles, η: quantum efficiency of a light receptor of an eye: 0.3, p: photon conversion coefficient (ORT) of a light source: 1.24 (liquid crystal is also acceptable), E: retina illumination (Troland): 50 $(cdm^2) \times r^2 \pi$ (mm)$=50r^2\pi$(td) (r: pupil radius) 100 or less, $\phi_0$: spectral density of nervous system noise: $3 \times 108$ sec·$deg^2$, $u_0$: spatial frequency of side suppression: 7 cycles/deg. By using this expression, not the contrast sensitivity by the eye optical system, but the contrast sensitivity of the whole optic system including other elements (for example, nervous system) can be predicted.

Figure 15:
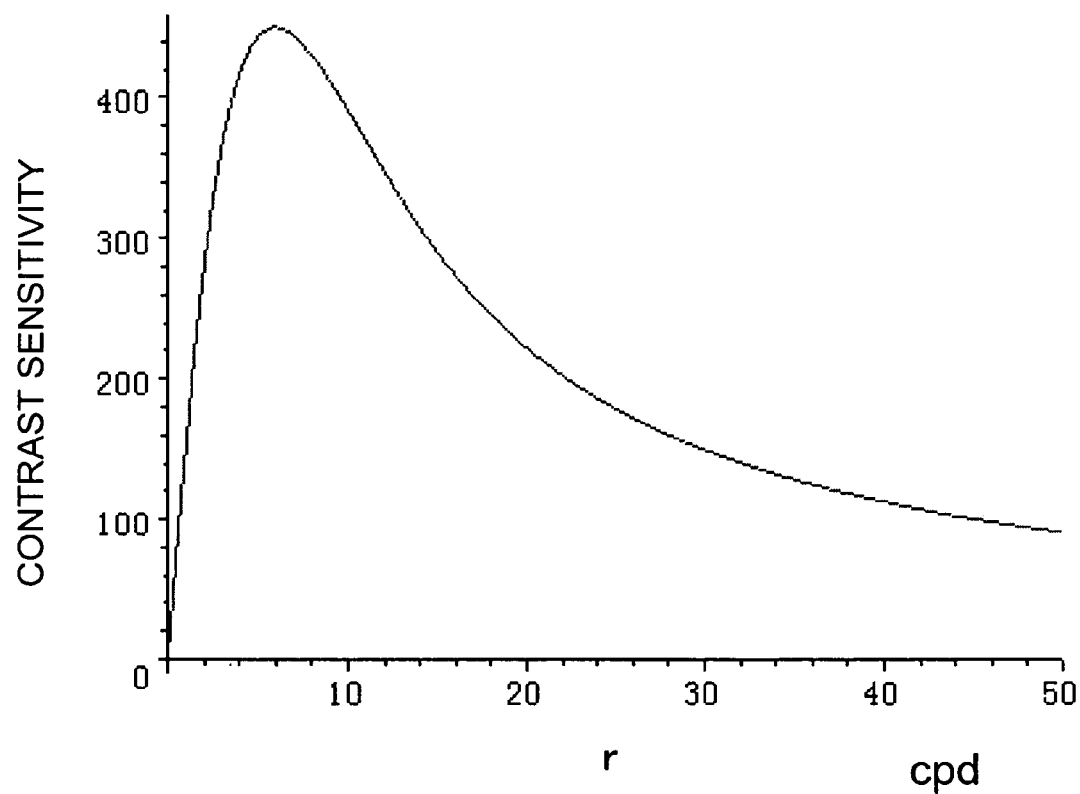
FIG. 15 is an explanatory view of contrast sensitivity.

FIG. 15 is an explanatory view of the contrast sensitivity. In the graph shown in FIG. 15, the vertical axis indicates the contrast sensitivity calculated by using the foregoing expression, and the horizontal axis indicates the spatial frequency, and the graph is a one-dimensional graph (graph at the time of, for example, s=0) on a certain section passing through the origin. By obtaining the contrast sensitivity of the whole optic system corresponding to the spatial frequency, for example, the visibility of a stripe index can be predicted.

Besides, an eye doctor or the like can compare, for example, the contrast sensitivity displayed on the display section with the sensitivity by subjective measurement. For example, it is possible to compare the sensitivities of 3 cpd, 6 cpr, 9 cpd and 12 cpd in the x direction obtained by general subjective measurement and according to vertical stripe indexes with the contrast sensitivities corresponding to the respective spatial frequencies at the time of s=0. Incidentally, since the contrast sensitivity does not depend on the angle in the case where it is displayed in polar coordinates and is rotation symmetry, it can also be displayed while the horizontal axis of the graph is made the amplitude component of the polar coordinate display.

Incidentally, the foregoing first, second, third, and fourth flowcharts and the calculation of the contrast sensitivity are combined and are used to obtain the correction values of the spherical power, the astigmatic power, and the astigmatic axis, and the visual acuity and/or the sensitivity at the time of the correction may be measured. In the case where the astigmatism is considered, since the spherical power calculated by the first flowchart becomes an equivalent spherical power $S_E$, the spherical power is made $S=S_E-(1/2)C$.

Figure 23:
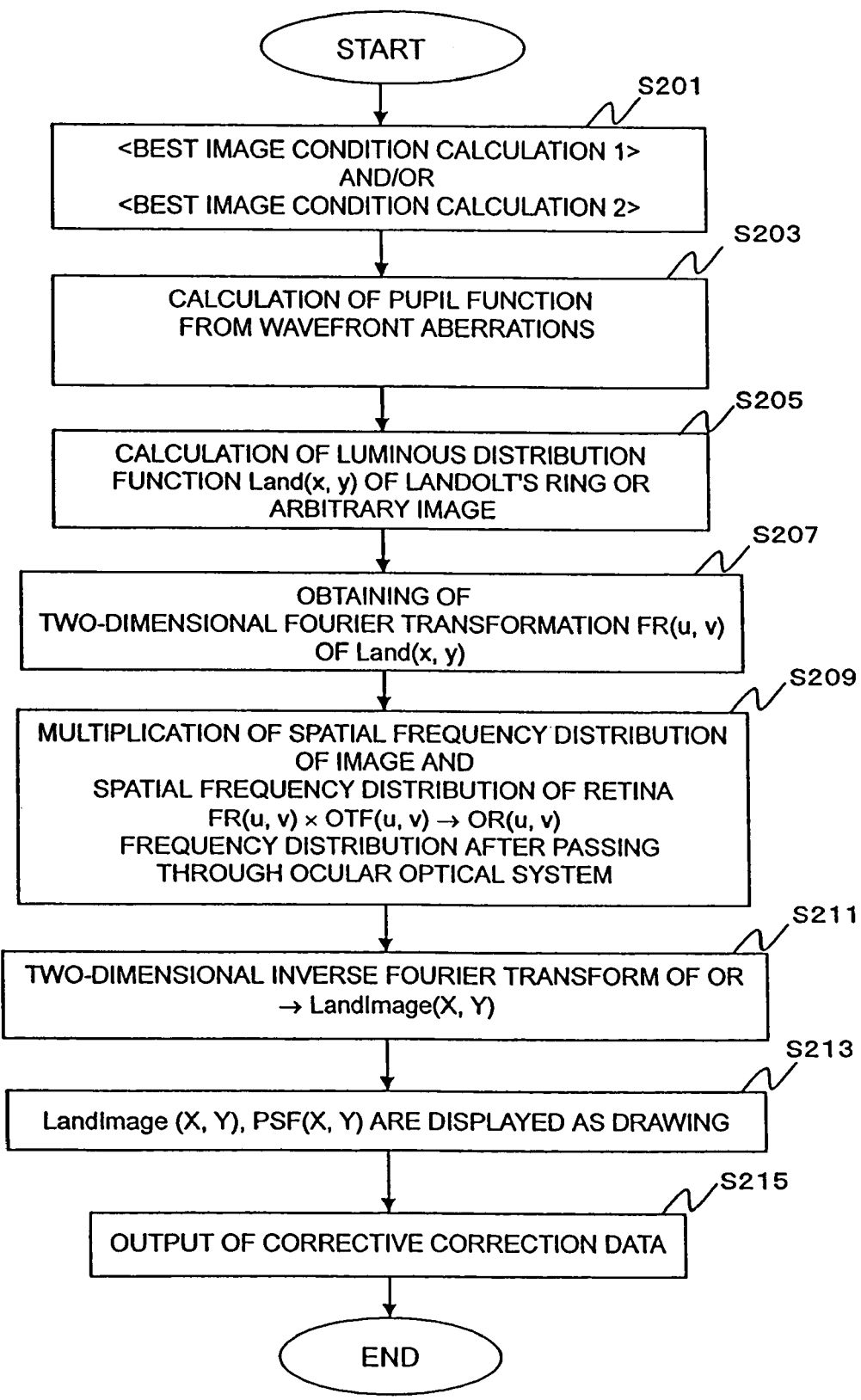
FIG. 23 is a flowchart of correction image simulation.

6. Correction Image Simulation 6-1 First Flowchart of Correction Image Simulation FIG. 23 is a flowchart of the correction image simulation of the step S107.

The arithmetic part 210 calculates a best image condition (S201). As described later, the details are such that the arithmetic part 210 obtains a lower order Zernike coefficient so that the Strehl ratio becomes maximum or the phase shift becomes as small as possible, and obtains corrective correction data. As the corrective correction data, suitable can be named among, for example, coefficients corresponding to defocus, astigmatism components, S, C, A, higher order spherical aberrations, higher order astigmatism aberrations, higher order coma aberrations, the Strehl ratio and the like.

The arithmetic part 210 obtains the wavefront aberrations $W(x, y)$ at the time of the best image condition, and calculates the pupil function $f(x, y)$ from $W(x, y)$ by the following expression (S203). Detail description of processes from step S205 to S211 is omitted, because each steps are same or similar to same number of steps of FIG. 8.

The arithmetic part 210 displays the LandImage(X, Y) and PSF(X, Y) on the display part 230 by a suitable display method of a drawing, graphic data, a graph and/or a numerical value, and suitably stores the data in the memory 240 (S213). The arithmetic part 210 reads out corrective correction data from the memory 240 as the need arises, and outputs it to the display part 230 (S215).

6-2 Calculation of Correction Data Based on Strehl Ratio

Figure 24:
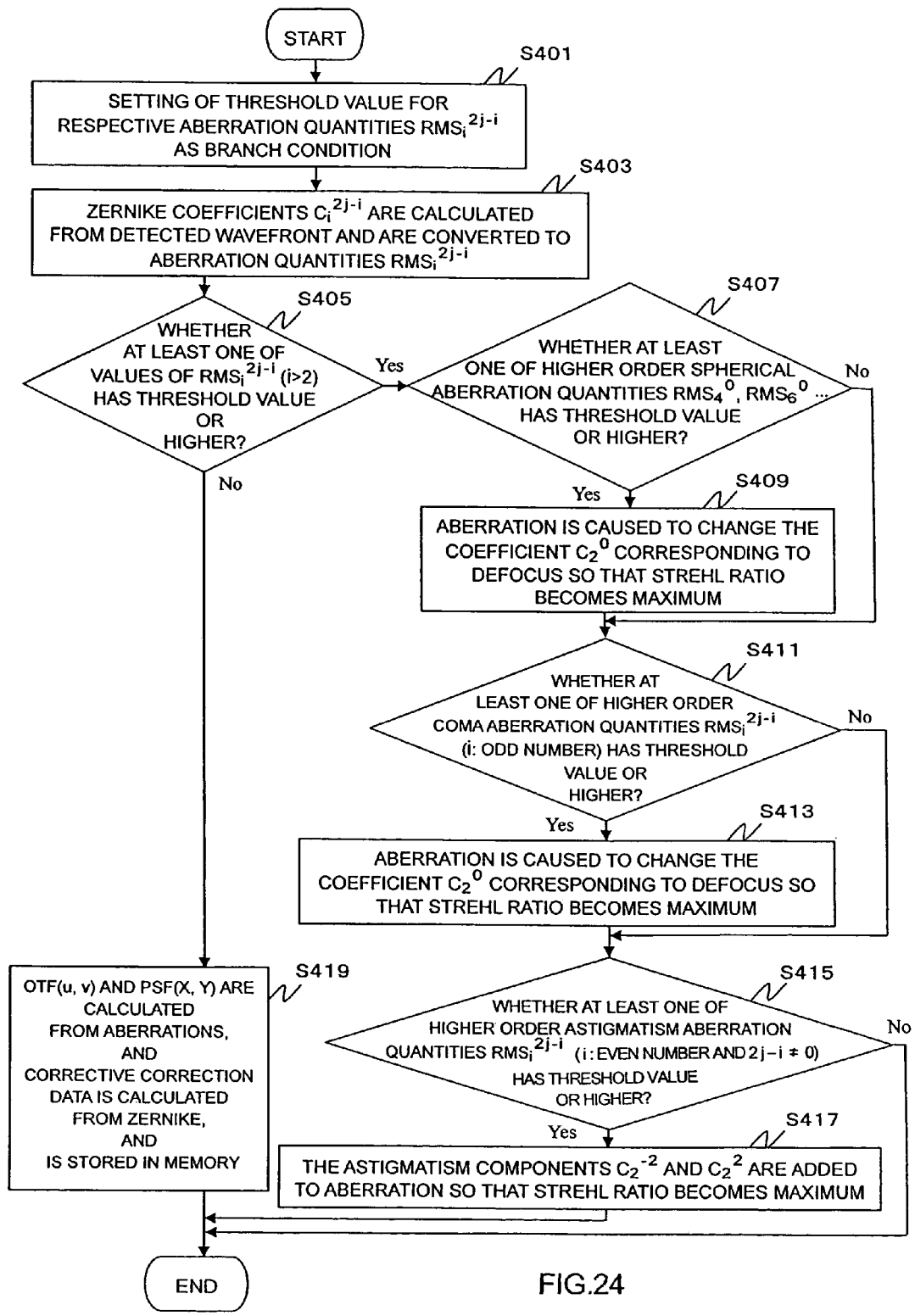
FIG. 24 is a flowchart concerning a first example of best image condition calculation.

FIG. 24 shows a flowchart concerning a first example of best image condition calculation. FIG. 24 is the detailed flowchart concerning the foregoing step S201.

First, the arithmetic part 210 sets a threshold value for respective aberration quantities $RMS_i^{2j-i}$ as a branch condition (S401). For example, this threshold value can be made a sufficiently small value (for example, 0.1) of aberration. The arithmetic part 210 calculates the Zernike coefficients $C_i^{2j-i}$ from the measured detection wavefront, and converts them to the aberration quantities $RMS_i^{2j-i}$ by the following expression (S403).

$$RMS_i^{2j-i} = \sqrt{\frac{\varepsilon_i^{2j-i}}{2(i+1)}} \, C_i^{2j-i} \quad (18)$$

$$(\varepsilon_i^{2j-i} = 2 \ (2j=i), \varepsilon_i^{2j-i} = 1 \ (2j \neq i))$$

The arithmetic part 210 judges whether at least one of the values of $RMS_i^{2j-i}$ (i>2) is the threshold value or higher (S405). Here, in the case where a judgment of No is made, it proceeds to step S419. On the other hand, here, when a judgment of Yes is made, the arithmetic part 210 carries out a next processing.

That is, the arithmetic part 210 judges whether at least one of the higher order spherical aberration quantities $R_4^0$, $R_6^0$ ... of aberration quantities RMS ($R_i^{2j-i}$) is the threshold value or higher (S407). Here, in the case of Yes, the arithmetic part 210 causes the aberration to change a coefficient ($C_2^0$) corresponding to the defocus so that the Strehl ratio becomes maximum (S409), and on the other hand, in the case of No, it proceeds to step S411. Next, the arithmetic part 210 judges whether at least one of the asymmetrical higher order coma aberration quantities $RMS_i^{2j-i}$ (i: odd number) is the threshold value or higher (S411). Here, in the case of Yes, the arithmetic part 210 causes the aberration to change the coefficient ($C_2^0$) corresponding to the defocus so that the Strehl ratio becomes maximum (S413), and on the other hand, in the case of No, it proceeds to step S415. Further, the arithmetic part 210 judges whether at least one of the higher order astigmatism aberration quantities $RMS_i^{2j-i}$ (i: even number and $2j-1 \approx 0$) is the threshold value or higher (S415). Here, in the case of Yes, the arithmetic part 210 adds astigmatism components ($C_2^{-2}$, $C_2^2$) to the aberration so that the Strehl ratio becomes maximum (S417), and on the other hand, in the case of No, it proceeds to step S419.

In this way, the arithmetic part 210 calculates OTF(u, v) and PSF(X, Y) from the aberrations, and further calculates the corrective correction data (suitable data such as coefficients corresponding to the defocus, astigmatism components, S, C, A, higher order spherical aberrations, higher order astigmatism aberrations, higher order coma aberrations, and Strehl ratio) from the Zernike coefficients, and stores them in the memory 240 (S419).

Incidentally, in order to correct only a desired component among the defocus and the astigmatism components, any of the pairs of the steps S407 and S409, the steps S411 and S413, and the steps of S415 and S417 may be omitted, or a step may be added to correct suitable higher order aberrations or Zernike coefficients other than these. For example, in the case where a fourth-order spherical aberration is mainly included in the higher order aberrations, the corrective correction data can be obtained by correcting in the direction in which the defocus quantity corresponding to the lower order aberrations are increased.

Next, the detailed processing of the steps S409, S413 and S417 will be described. In the respective steps, the arithmetic part 210 carries out the processing as follows.

In order to obtain a more suitable image plane, the arithmetic part 210 adds to the wavefront aberrations $W(x, y)$ the lower order Zernike coefficients $C_i^{2j-i}$ ($1 \leq i \leq 2$) at each step presently noted for the aberration quantities comparable to the higher order aberration quantities according to the threshold value of the last noted higher order aberration quantities ($RMS_4^0$, $RMS_6^0$ ... ) in the flow. For example, $C_2^0$ is added at the step S409; $C_2^0$, at the step 413; and $C_2^{-2}$, $C_2^2$, at the step S417.

Further, the pupil function $f(x, y)$ is obtained from the wavefront aberrations in the manner described below.

$$f(x,y)=e^{ikW(x,y)}$$

(i: imaginary number, k: wave number vector ($2\pi/\lambda$), $\lambda$: wavelength) The arithmetic part 210 performs the Fourier transformation on this pupil function $f(x, y)$, so that an amplitude distribution U(u, v) of a point image is obtained as in the following expression.

$$\text{amplitude } U(u, v) = \int\int_{-\infty}^{\infty} f(x, y)\exp\left[-\frac{i}{R}\frac{2\pi}{\lambda}(ux + vy)\right]dxdy \quad (19)$$

($\lambda$: wavelength
R: a distance from a pupil to an image point (retina)
(u, v): a coordinate value on a plane orthogonal to an optical axis while an image point O is made the origin
(x, y): a coordinate value on a pupil plane)

The arithmetic part 210 multiplies U(u, v) by its complex conjugate and obtains I(u, v) as a point image intensity distribution (PSF) by the following expression.

$$I(u,v)=U(u,v)U^*(u,v)$$

Besides, when the center intensity of PSF at the time when there is no aberrations (W(x, y)=0) is made Io(0, 0), the Strehl ratio is defined as follows:

Strehl ratio=$I(0, 0)/Io(0, 0)$.

In the first example, the arithmetic part 210 recursively or analytically obtains a value of the lower order Zernike coefficient $C_{ij}$ ($1 \leq i \leq 2$) so that the value of the Strehl ratio becomes maximum.

6-3 Calculation of Correction Data Based on a Phase Shift

Figure 25:
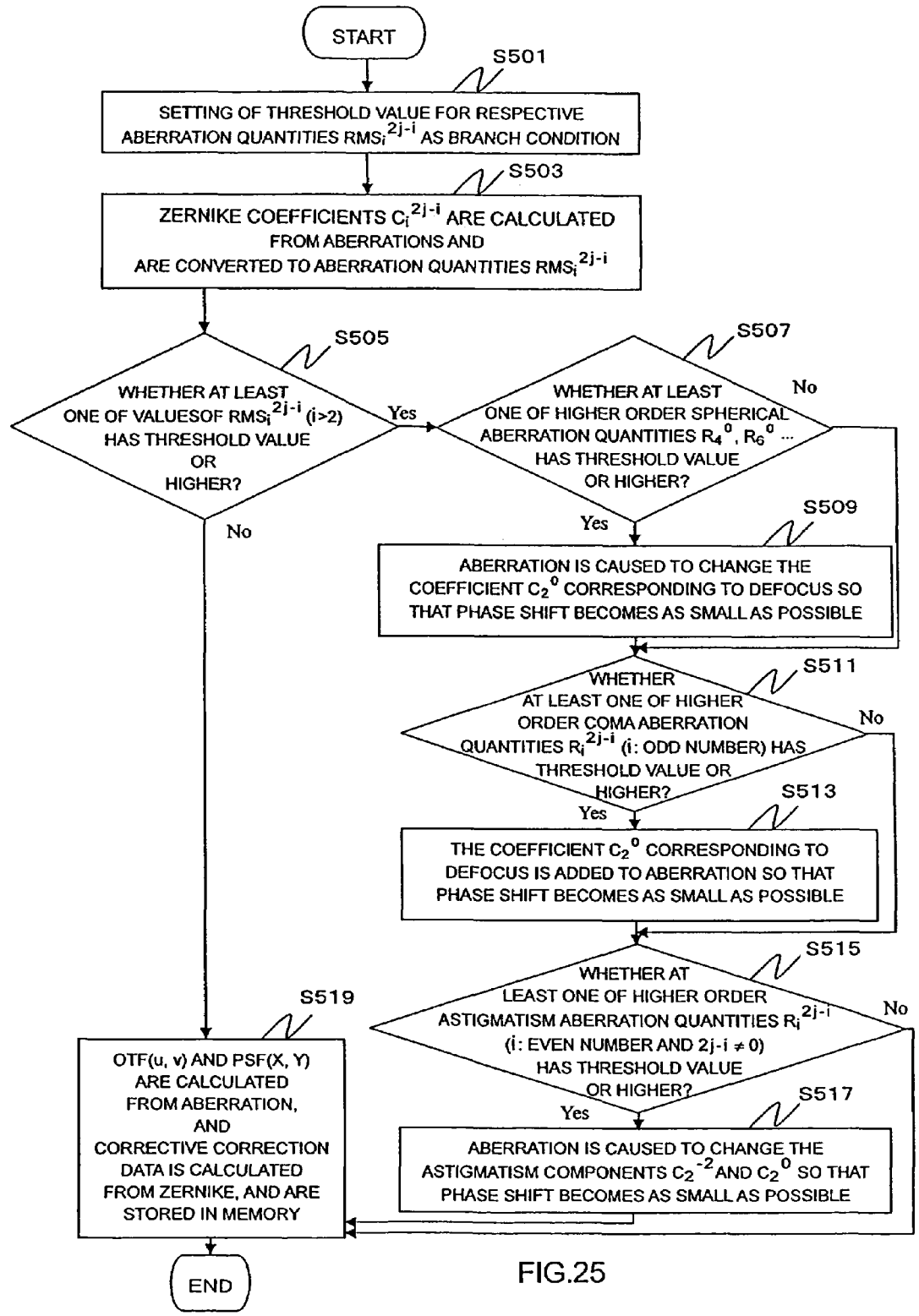
FIG. 25 is a flowchart concerning a second example of best image condition calculation.

Next, FIG. 25 is a flowchart concerning the second example of the best image condition calculation.

First, the arithmetic part 210 sets a threshold value for the respective aberration quantities $RMS_i^{2j-1}$ as a branch condition (S501). For example, this threshold value is made a sufficiently small value (for example, 0.1) of aberration.

The arithmetic part 210 calculates the Zernike coefficients $C_i^{2j-1}$ from the measured detection wavefront, and converts them to the aberration quantities $RMS_i^{2j-1}$ by the expression indicated in the first example (S503). The arithmetic part 210 judges whether at least one of $RMS_i^{2j-1}$ (I >2) is the threshold value or higher (S505). Here, in the case of the judgment of No, it proceeds to step S519. On the other hand, in the case of the judgment of Yes, the arithmetic part 210 carries out a next processing.

That is, the arithmetic part 210 judges whether at least one of the higher order spherical aberration quantities $R_4^0$, $R_6^0$ . . . is the threshold value or higher (S507). Here, in the case of Yes, the arithmetic part 210 causes the aberration to change the coefficient ($C_2^0$) corresponding to the defocus so that the phase shift becomes as small as possible (S509), and on the other hand, in the case of No, it proceeds to step S511. Next, the arithmetic part 210 judges whether at least one of the higher order coma aberration quantities $RMS_i^{2j-1}$ (i: odd number) is the threshold value or higher (S511). Here, in the case of Yes, the arithmetic part 210 causes the aberration to change the coefficient ($C_2^0$) corresponding to the defocus so that the phase shift becomes as small as possible (S513), and on the other hand, in the case of No, it proceeds to step S515. Further, the arithmetic part 210 judges whether at least one of the higher order astigmatism aberration quantities $RMS^{i2j-1}$ (i: even number and j$\neq$0) is the threshold value or higher (S515). Here, in the case of Yes, the arithmetic part 210 adds the astigmatism components ($C_2^{-2}$, $C_2^2$) to the aberration so that the Strehl ratio becomes maximum (S517), and on the other hand, in the case of No, it proceeds to step S519.

In this way, the arithmetic part 210 calculates OTF(u, v) and PSF(X, Y) from the aberrations, and further calculates the corrective correction data (suitable data such as the coefficients corresponding to the defocus, astigmatism components, S, C, A, higher order spherical aberrations, higher order astigmatism aberrations, higher order coma aberrations, and Strehl ratio) from the Zernike coefficients, and stores them in the memory 240 (S519).

Incidentally, any of the pairs of the steps S507 and S509, the steps S511 and S513, and the steps S515 and S517 may be omitted so that only a desired component is corrected among the defocus and the astigmatism components. Besides, a step may be added so that suitable higher order aberrations or Zernike coefficients other than these is corrected.

Next, the detailed processing of the steps S509, S513 and S517 will be described. The arithmetic part 210 carries out the processing as follows.

First, as described in the detailed processing of the steps S409, S413 and S417, the arithmetic part 210 obtains the point image intensity distribution (PSF) from the expression of the wavefront at the time of the objective complete correction calculated from the Zernike coefficients. Next, the arithmetic part 210 performs a Fourier transformation (or autocorrelation) on the PSF to normalize it as in the following expression and obtains OTF.

$$R(r, s) = \int\int_{-\infty}^{\infty} I(u, v)e^{-i2\pi(ru+sv)}dudv \quad (20)$$

(r, s: a variable of a spatial frequency region)

$$OTF = \frac{R(r, s)}{R(0, 0)}$$

In general, the amplitude of a spatial frequency region and a phase distribution R(r, s) become complex numbers, and when its real number part is A(r, s), and its imaginary part is B(r, s), $$R(r, s)=A(r, s)+iB(r, s)$$

and the shift of the phase (phase shift, PTF) is calculated by $$\phi(r, s) = \tan^{-1}\frac{B(r, s)}{A(r, s)} \quad (21)$$

In the second example, the arithmetic part 210 recursively and analytically obtains such a value of the lower order Zernike coefficient $C_i^{2j-1}$ that a value at which the R(r, s) has an extreme value is brought to a high frequency to the extent possible, that is, the phase shift becomes as small as possible.

Incidentally, with respect to the first example and the second example of the best image condition calculation, both the processings may be carried out to obtain such a condition that the Strehl ratio is large, and the phase shift is small.

7. Display Example 7.1 Display Example at the Time of Visual Acuity Measurement

Figure 16:
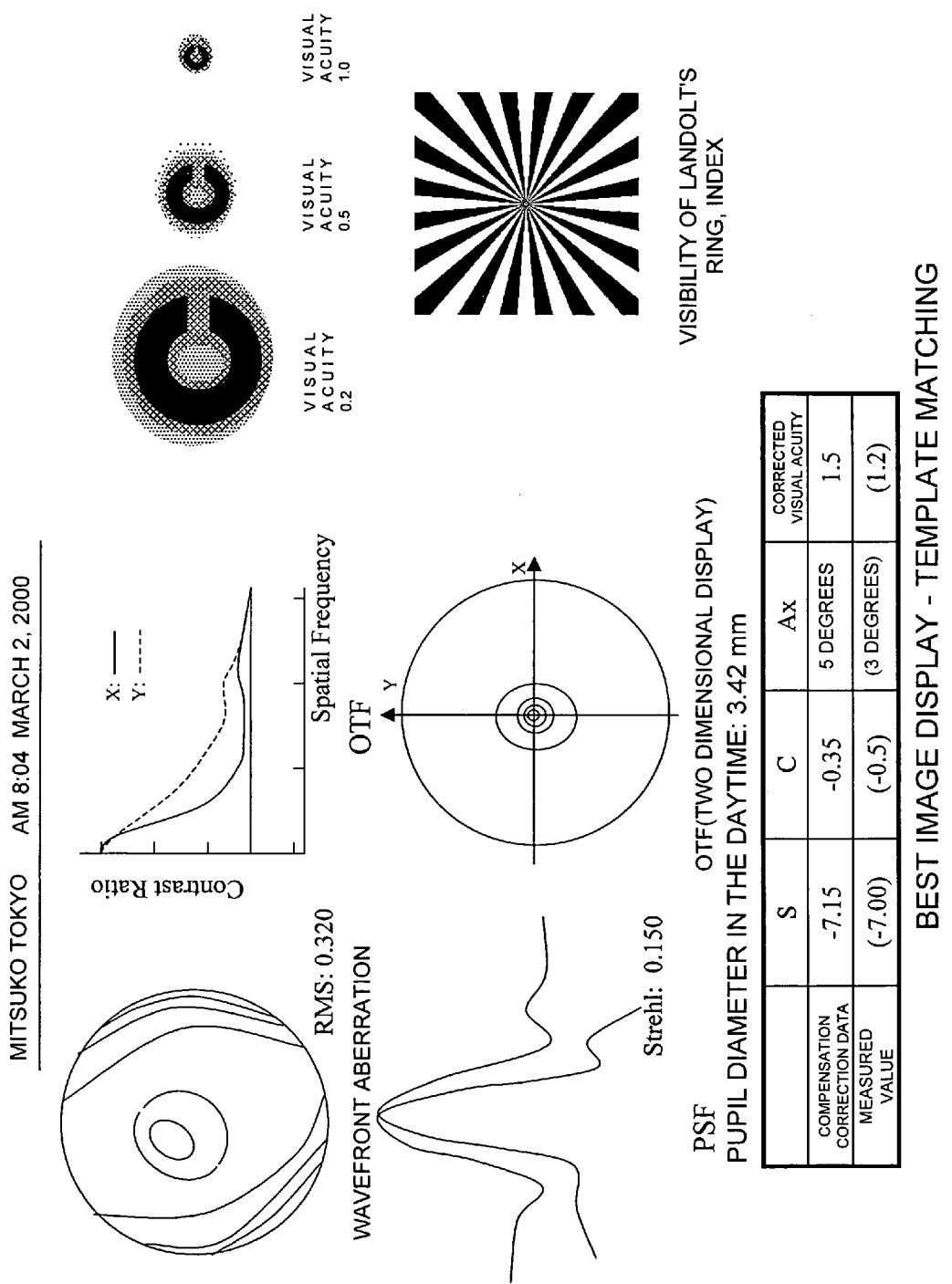
FIG. 16 shows a display example of visual acuity estimation by template matching.

FIG. 16 shows, with respect to the best image display-template matching and as numerical data, the spherical power S, astigmatic power C, and astigmatic axis angle Ax, which are compensation correction data, the pupil diameter, and the spherical power S, astigmatic power C, astigmatic axis angle Ax, and corrected visual acuity, which are measured values before the compensation correction. Further, corrected visual acuity in the correction data may be displayed. In this example, since the component of the higher order aberration has a predetermined value or more, a difference in numerical value occurs between the compensation correction data and the measured values. In these drawings, the wavefront aberration, PSF, OTF, OTF (two-dimensional display), S, C, Ax, Landolt's ring, visibility of the index and the like are displayed on the display section 230. Further, for example, the contrast sensitivity shown in FIG. 15 may be displayed on the display section 230. Besides, some of them may be suitably selected and displayed.

Figure 17:
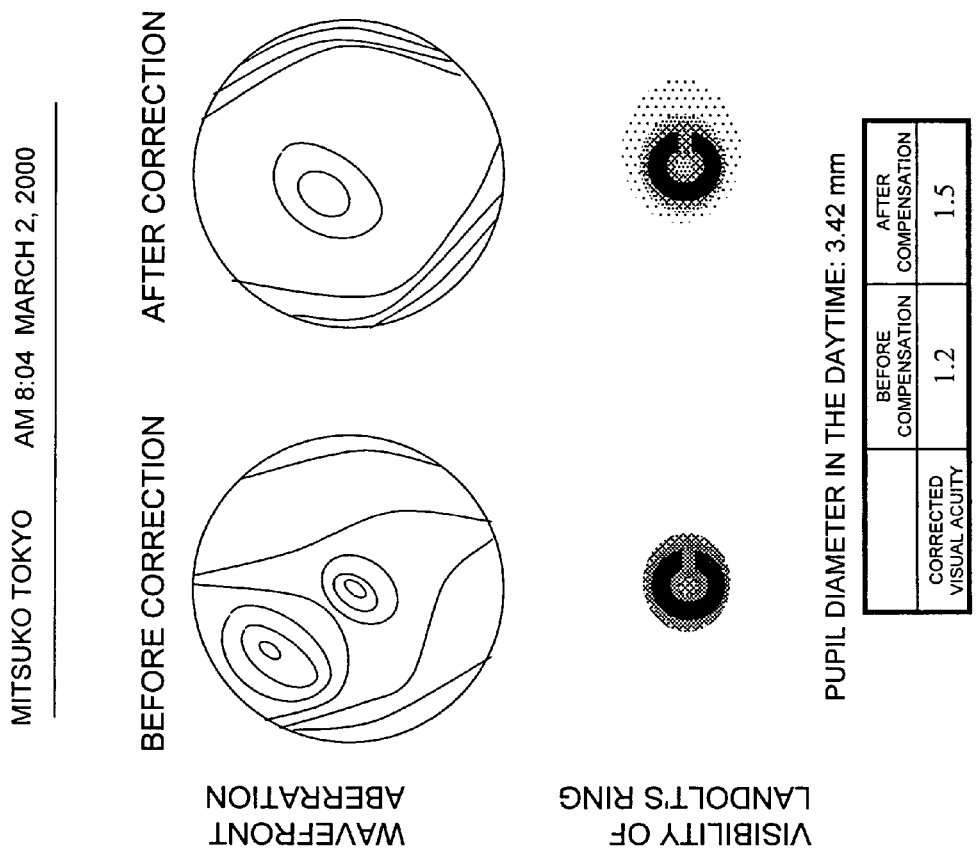
FIG. 17 shows a display example concerning comparison between pre-compensation and post-compensation.

FIG. 17 is a view showing a display example concerning the comparison between pre-compensation and post-compensation. This drawing shows the corrected visual acuity, wavefront aberration, and visibility of the Landolt's ring, which are obtained before and after the compensation, and the pupil diameter. As shown in the drawing, it is indicated that after the compensation correction, the wavefront aberration becomes relatively uniform, and the Landolt's ring is relatively well seen. Besides, the corrected visual acuity of the subjective eye under an environment after the compensation correction is shown.

FIG. 18 is an explanatory view of an example of prescription data for eyeglasses/contacts. FIG. 19 is an explanatory view of an example of data for refractive surgery.

The respective data are stored in the memory 240 from the calculation section 210, and/or displayed on the display section 230. This example indicates that in the data of the case where the refractive surgery is performed while only the SCA is made the compensation correction data, the corrected visual acuity is improved by performing the correction in such a way that the value of S in the compensation correction data is intensified, the value of C is weakened, and the axial direction of A is slightly changed. Besides, FIG. 19 shows expected values of the respective parameters under the illustrated pupil diameter after the compensation correction.

FIG. 20 is an explanatory view of an example of prescription data for eyeglasses/contacts when the environmental condition is changed. For example, the pupil diameter of the eye 60 to be measured is measured in the illumination states corresponding to the respective environmental conditions, and the correction data and corrected visual acuities at the respective pupil diameters are displayed. It is indicated that the compensation correction data slightly varies according to the pupil diameter. That is, it is indicated that the optimum prescription value varies according to the environment of the subjective eye. Besides, for example, the doctor considers the environment of the subjective eye, and can select the prescription value. Incidentally, the environmental conditions to be displayed can be suitably changed.

In the example shown in FIG. 20, although the correction data corresponding to the respective environmental conditions are obtained, and the visual acuities under the environmental conditions are displayed, the visual acuity under another environmental condition can also be estimated and displayed. For example, in the case where correction is made by the compensation correction data in the daytime, the visual acuities in the daytime, under a fluorescent lamp and in a room and daytime can also be predicted and displayed.

FIG. 21 is an explanatory view of an example of pupil data when the environmental condition is changed. For example, the pupil diameter of the eye 60 to be measured is measured under illumination states corresponding to the respective environmental conditions, and the shift amount (x direction, y direction) from the limbus center of the pupil center at the respective pupil diameters and the corrected visual acuity are shown. It is indicated that the pupil center is shifted by the change of the environmental condition, and the center (origin) at the time of analysis is shifted.

FIG. 22 is a comparison view of prescription data for eyeglasses/contacts and measurement at constant pupil diameters. There are shown, for example, the correction data and corrected visual acuities in the case where similarly to the conventional measurement, the pupil diameter is made 4 mm and 6 mm and the case where the pupil diameter is measured (for example, under illumination of 50 1x). The correction data and corrected visual acuity slightly vary between the case where the pupil diameter is fixed and the case where it is measured. Incidentally, although FIG. 21 shows, as an example, data using the pupil diameter under the illuminated of 50 1x, it is possible to estimate the visual acuity of the subjective eye under an appropriate environment by suitably changing the illumination condition.

Incidentally, in the foregoing drawing, although the visual acuity is expressed by the decimal visual acuity, it may be displayed by the logMAR visual acuity. Besides, the condition to be displayed can be suitably changed.

7.2 Display Example in Correction Data Simulation

Figure 26:
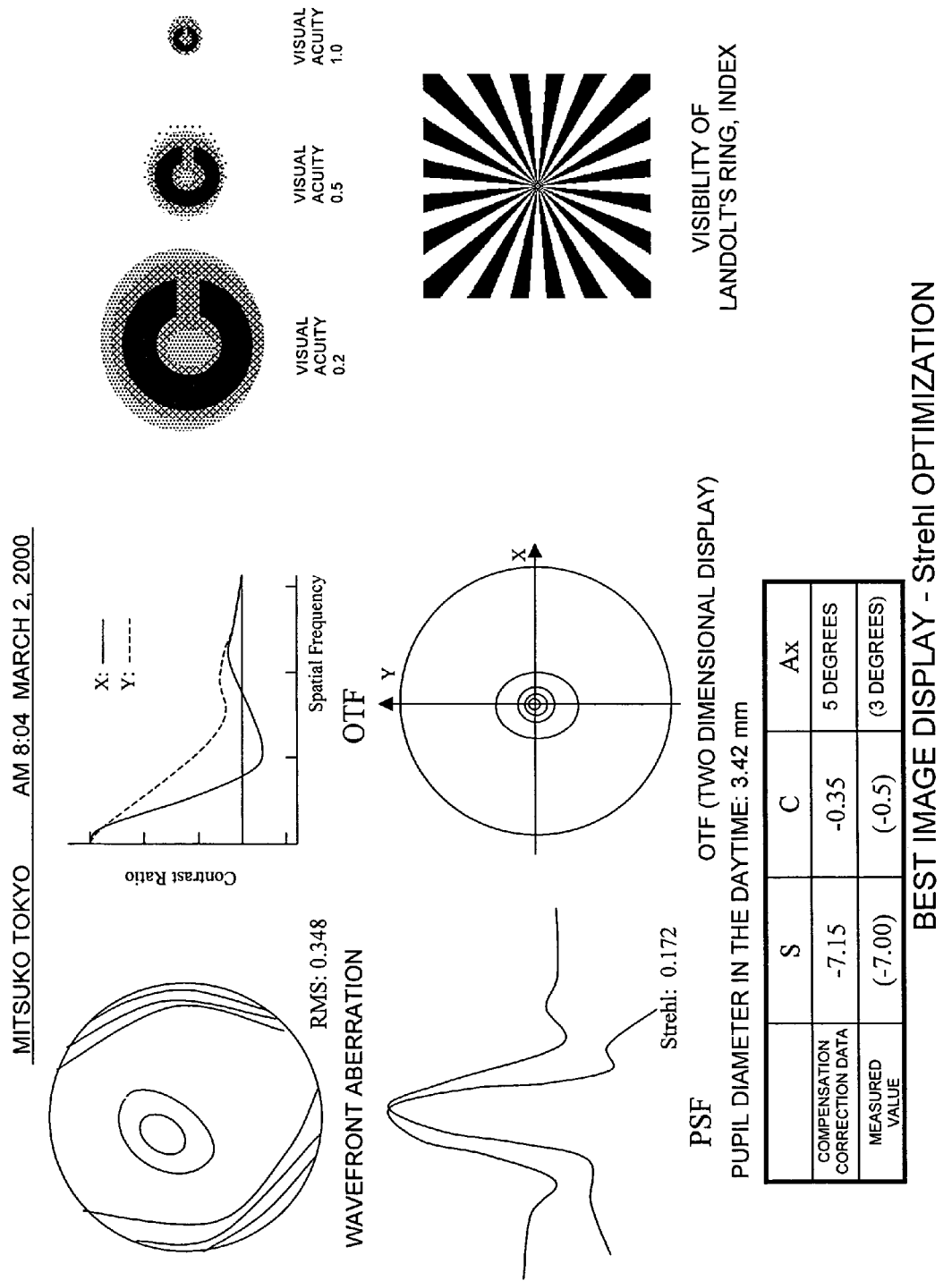
FIG. 26 is a view showing a display example of best image display-Strehl ratio optimization.

FIG. 26 shows, with respect to the best image display-Strehl optimization and as numerical data, the spherical power S, astigmatic power C, and astigmatic axis angle Ax, which are compensation correction data, the spherical power S, astigmatic power C, and astigmatic axis angle Ax, which are measured values before the compensation correction, and the pupil diameter used for the calculation of the correction data. In this example, since the components of the higher order aberrations have predetermined values or more, a difference in numerical value occurs between the compensation correction data and the measured values.

Figure 27:
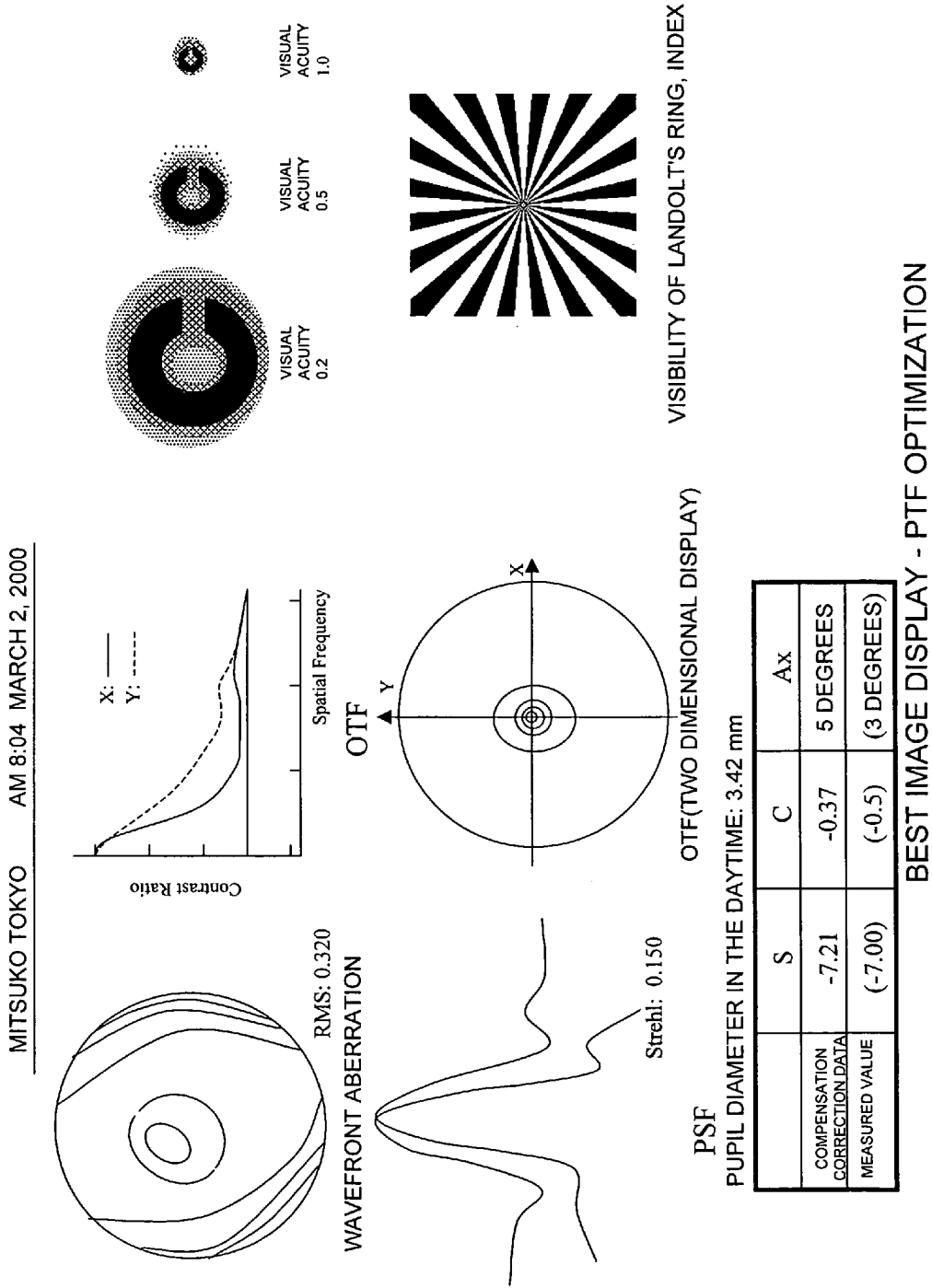
FIG. 27 is a view showing a display example of best image display-PTF optimization.

FIG. 27 shows, with respect to the best image display-PTF optimization and as numerical data, the spherical power S, astigmatic power C, and astigmatic axis angle Ax, which are compensation correction data, the spherical power S, astigmatic power C, and astigmatic axis angle Ax, which are measured values before the compensation correction, and the pupil diameter used for the calculation of the correction data. In this example, since the components of the higher order aberrations have predetermined values or more, a difference in numerical value occurs between the compensation correction data and the measured values.

Figure 28:
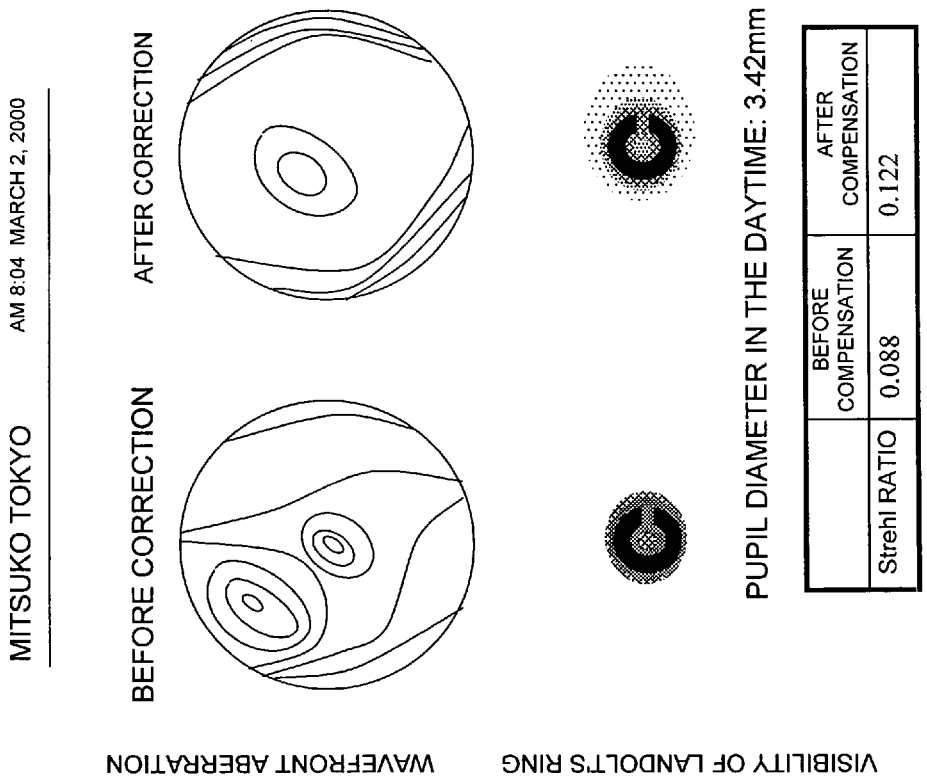
FIG. 28 is a view showing a display example concerning comparison between pre-compensation and post-compensation.

FIG. 28 is a view showing a display example concerning the comparison between pre-compensation and post-compensation. This drawing shows the wavefront aberrations before and after the compensation, the visibilities of the Landolt's ring, Strehl ratios, and the pupil diameter. As shown in the drawing, the Strehl ratio after the compensation is higher, the wavefront aberrations become relatively uniform, and the Landolt's ring can also be relatively well seen.

FIG. 29 is an explanatory view of an example of prescription data for eyeglasses/contacts. FIG. 30 is an explanatory view of an example of data for refractive surgery.

The respective data are stored from the calculation section 210 into the memory 240, and/or are displayed on the display section 230. This example indicates that in the data of the case where the refractive surgery is performed while only the SCA are made the compensation correction data, the Strehl ratio becomes high and the correction effect becomes high by performing the correction in such a manner that the value of S in the compensation correction data is intensified, the value of C is weakened, and the axial direction of A is slightly changed.

FIG. 31 is an explanatory view of an example of prescription data for eyeglasses/contacts when the environmental condition is changed. For example, the pupil diameters of the eye 60 to be measured are measured under illumination states corresponding to the respective environmental conditions, and the correction data at the respective pupil diameters are displayed. It is indicated that the compensation correction data slightly varies according to the pupil diameters. That is, it is indicated that the optimum prescription value varies according to the environment of the subjective eye. Besides, for example, the doctor or the like considers the environment of the subjective eye, and can select the prescription value. Incidentally, the environmental condition to be displayed can be suitably changed.

Figure 32:
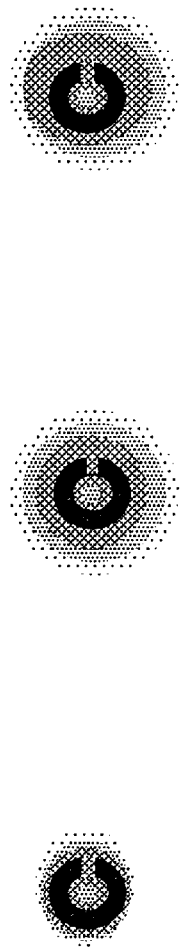
FIG. 32 is a comparison view of prescription data for eyeglasses/contacts with respect to measurement with a constant pupil diameter.

FIG. 32 is a comparison view of prescription data for eyeglasses/contacts and measurement at constant pupil diameters. For example, correction data when the pupil diameter is made 4 mm and 6 mm similarly to the conventional measurement, and correction data of the case where the pupil diameter is measured (for example, under illumination of 50 1x) are displayed. The correction data slightly varies between the case where the pupil diameter is fixed and the case where it is measured. In this embodiment, it is possible to obtain the optimum correction data corresponding to the pupil diameter of the subjective eye. Incidentally, the condition to be displayed can be suitably changed.

8. Modified Example

A modified example of the invention will be described below.

This modified example modifies the calculation method of the best image condition at S201 of FIG. 23.

A component of an i-th row and a j-th column of Jacobian matrix A is $$A_{ij} = \frac{\partial f_i(x)}{\partial x_j} \quad (22)$$

Where, $f_i(x)$ is the Strehl ratio, the PTF corresponding to a suitable frequency, or some values of the PTF corresponding to plural frequencies. Besides, it may be a combination of the Strehl ratio and the PTF. Besides, a vector x is an adjustable parameter, and here, the sphere (or defocus corresponding to that) and two astigmatisms correspond to that.

The calculation expressions of the Strehl ratio and the PTF are already given. The ideal value of the Strehl ratio is 1. It is assumed that the following expression expresses the Strehl ratio.

$$f_1(x) = f_S(hc, c_2^0, c_2^{-2}, c_2^2) \quad (23)$$

Where, $f_1$ denotes the expression of the same indication in the expression (22).

Besides, for example, as the PTF, values corresponding to the spatial frequency of 3 cpd, 6 cpd, 12 cpd, and 18 cpd are taken, and it is ideal that this is 0.

$$f_2(x) = f_{PTF3}(hc, c_2^0, c_2^{-2}, c_2^2) \quad (24)$$

$$f_3(x) = f_{PTF6}(hc, c_2^0, c_2^{-2}, c_2^2) \quad (25)$$

$$f_4(x) = f_{PTF12}(hc, c_2^0, c_2^{-2}, c_2^2) \quad (26)$$

$$f_5(x) = f_{PTF18}(hc, c_2^0, c_2^{-2}, c_2^2) \quad (27)$$

In the expressions (23), (24), (25), (26) and (27), hc denotes a vector of higher order aberration coefficients, $c_2^0$ denotes a coefficient of a defocus term relating to the sphere, $c_2^{-2}$ and $c_2^2$ denote coefficients of terms relating to astigmatism. The vector hc is given by wavefront aberration measurement, and here, it is constant. Thus, the remaining three coefficients are made a parameter vector x and are suitably moved to guide $f_s$ to the minimum value, which is a task here.

Here, the partial differentiation of the expression (22) can be calculated by slightly moving the parameters to prepare a change table, and the Jacobian matrix in this system is obtained.

Now, when the task here is expressed in other words again, since nonlinear optimization in the case where the Jacobian, that is, the partial differential coefficient is known has only to be performed, when optimizing algorism of a Newton method system is used, it is easy to obtain a solution since the example is simple. When a specific solution according to a corrected Marquardt method is stated, a correction vector $\Delta x$ can be obtained by $$(A^t W A + \lambda I)\Delta x = A^t W(y - f(x)) \quad (28)$$

Here, t at the shoulder of the matrix denotes a transposed matrix, and W denotes a weighting matrix. The first element of y corresponds to Strehl ratio, and the remainder corresponds to four components of PTF, it has only to be made $(1,0,0,0,0)^t$. $\lambda$ is called a damping factor, and it is made large at first, and then, it is made small in accordance with going of optimization.

$$W = \begin{pmatrix} w_1 & 0 & 0 & 0 & 0 \\ 0 & w_2 & 0 & 0 & 0 \\ 0 & 0 & w_3 & 0 & 0 \\ 0 & 0 & 0 & w_4 & 0 \\ 0 & 0 & 0 & 0 & w_5 \end{pmatrix} \quad (29)$$

A subscript corresponds to a subscript of f. Weighting suitable for the object of a prescription can be freely performed, for example, when the Strehl ratio is desired to be selectively optimized, $w_1$ is made large. The expression (7) is applied several times, and when $$S = W(y - f(x)) \quad (30)$$

becomes suitably small (when a conversion condition is satisfied), the calculation is stopped, and x at that time is made the solution. By this, the optimum the sphere (or defocus corresponding to that) and two astigmatisms are obtained.

Incidentally, the best image condition calculation can also be performed by finding out the position where the Strehl ratio becomes maximum or the phase shift (PTF) becomes substantially zero while the defocus amount and/or the astigmatism component is changed slightly. Besides, a position where the Strehl ratio becomes maximum or the phase shift (PTF) becomes substantially zero may be obtained by using a well-known Newton method.

9. Appendix

The apparatus and system of the ophthalmic data measurement according to the invention can be provided through an ophthalmic data measurement program for causing a computer to execute the respective procedures, a computer readable recording medium on which the ophthalmic data measurement program is recorded, a program product including the ophthalmic data measurement program and loadable into the internal memory of a computer, a computer, such as a server, including the program, or the like.

Besides, although the measurement data indicating the refractive power distribution of the eye to be measured is obtained by the optical system 100 shown in FIG. 1, no limitation is made to this, and the structure can be made by another aberrometer or the like.

INDUSTRIAL APPLICABILITY

According to the invention, the optical characteristic corresponding to the pupil diameter of the eye to be examined and the correction data close to the optimum prescription value are calculated, and more accurate measurement can be performed.

Besides, according to the invention, in the results of measurement by the eye characteristic measuring apparatus which can measure higher order aberrations, in the case where the higher order aberrations are included, the lower order aberrations corresponding to the time of the objective complete correction are not made the compensation correction data, and, for example, the optical performance is evaluated by the Strehl ratio or the phase shift, the lower order aberration amount to increase the Strehl ratio and/or to reduce the phase shift is calculated, and the compensation correction data, such as S, C, A, at that time are obtained, so that the correction data close to the optimum prescription value of eyeglasses/contacts can be obtained. Further, the simulation of the visibility of the index for eye examination is performed, and the appropriate correction element is obtained, so that it is also possible to obtain the correction data close to the subjective value.

According to the invention, the visual acuity of the eye to be examined can be estimated under the brightness (for example, in the daytime or in a room) corresponding to the environment of the subjective eye in daily life. Besides, according to the invention, in view of the pupil diameter of the eye to be examined in daily life, the visual acuity with respect to the index of high contrast and/or low contrast can be estimated. According to the invention, the contrast sensitivity in view of the pupil diameter can be predicted. Further, according to the invention, by using the pupil diameter under the brightness (for example, in the daytime or in a room) corresponding to the environment of the subjective eye, the correction data close to the optimum prescription value under the environment is obtained, and the visual acuity under the environment of the subjective eye can be estimated by the correction using the obtained correction data. Besides, the simulation of an index such as the Landolt's ring on the retina in view of the size of the pupil area calculated in the halfway process is also singly effective.

The invention claimed is:

1. An ophthalmic data measuring apparatus comprising:
   a first light source part to emit a light flux of a first wavelength;
   a first illuminating optical system for performing illumination to condense the light flux from the first light source part on a vicinity of a retina of an eye to be examined;
   a first light receiving optical system for receiving a part of the light flux reflected by and returning from the retina of the eye to be examined through a first conversion member to convert it into at least substantially 17 beams;
   a first light receiving part for receiving the received light flux of the first light receiving optical system; and
   a calculation section to perform Zernike analysis based on an inclination angle of the light flux obtained by the first light receiving part, to obtain an optical characteristic of the eye to be examined, and (1) to estimate one of or two or more of a visual acuity, the optical characteristic and a sensitivity of the eye to be examined under an observation condition corresponding to an environment of the eye to be examined, or (2) to calculate appropriate correction data suitable for the eye to be examined,
   wherein the calculation section comprises:
   first means for obtaining measurement data indicating a refractive power distribution of the eye to be examined and pupil data including a value of a pupil diameter of the eye to be examined or a pupil diameter image and for obtaining lower order aberrations and higher order aberrations based on an observation condition parameter including the measurement data and the pupil data;
   second means for calculating an evaluation parameter indicating quality of visibility by the eye to be examined based on the observation condition parameter and/or the obtained lower order aberrations and the higher order aberrations; and
   third means for, in accordance with the calculated evaluation parameter, (1) estimating one of or two or more of the visual acuity, the optical characteristic and the sensitivity, of the eye to be examined under the observation condition corresponding to the environment of a subjective eye or (2) calculating the appropriate correction data suitable for the eye to be examined by changing the lower order aberration.

2. The ophthalmic data measuring apparatus according to claim 1, wherein
   the pupil data is data corresponding to the observation condition in accordance with the environment of the subjective eye and/or
   the second means simulates the visibility of an image by the eye to be examined and calculates the evaluation parameter indicating the quality of the visibility.

3. The ophthalmic data measuring apparatus according to claim 1, wherein the first means is constructed to cause
   the calculation section to receive the measurement data indicating the refractive power distribution of the eye to be examined, and the pupil data including the pupil image at a time of measurement or under a correction environment in which the correction data is obtained, to calculate a pupil diameter under the observation condition or the correction environment based on the received pupil data, and to obtain the lower order aberrations and the higher order aberrations based on the received measurement data and the calculated pupil diameter.

4. The ophthalmic data measuring apparatus according to claim 1, wherein the first means comprises:
   means by which the calculation section receives the measurement data indicating the refractive power distribution of the eye to be examined and the pupil data including the pupil image at the time of measurement or under the correction environment;
   means by which the calculation section detects points on a pupil edge based on the received pupil data;
   means by which the calculation section calculates a focal point and a major axis and/or a minor axis of an ellipse fitted to the detected points;
   means by which the calculation section calculates the pupil diameter of the eye to be examined based on the major axis and/or the minor axis of the ellipse; and means by which the calculation section obtains the lower order aberrations and the higher order aberrations based on the received measurement data and the calculated pupil diameter.

5. The ophthalmic data measuring apparatus according to claim 1, further comprising:
a second light source to emit a light flux of a second wavelength;
a second illuminating optical system to illuminate a vicinity of a cornea of the eye to be examined with a predetermined pattern and by the second illumination light flux from the second light source;
a second light receiving optical system to receive the second illumination light flux reflected by and returning from the vicinity of the cornea of the eye to be examined;
a second light receiving part to receive the received light flux of the second light receiving optical system; and
a pupil data formation part to form pupil data of the eye to be examined from output of the second light receiving part,
wherein the calculation section is constructed to obtain the pupil data by the pupil data formation section.

6. The ophthalmic data measuring apparatus according to claim 1, further comprising an anterior ocular segment illuminating part constructed to be capable of illuminating an anterior ocular segment of the eye to be examined at desired brightness,
wherein the calculation section is constructed to adjust the anterior ocular segment illuminating part to produce brightness corresponding to a predetermined observation condition or correction environment, and to estimate the visual acuity of the eye to be examined and/or the sensitivity based on an output signal of the first light receiving part in the illumination state and the pupil data, or to obtain the appropriate correction data suitable for the eye to be examined.

7. The ophthalmic data measuring apparatus according to claim 6, wherein the anterior ocular segment illuminating part is constructed to perform measurement by sequentially changing the illumination state from a dark one to a bright one in a case where plural illumination states are formed.

8. The ophthalmic data measuring apparatus according to claim 1, wherein the second means comprises:
means by which the calculation section simulates the visibility of an index for eye examination by the eye to be examined before or after correction to form index image data;
means by which the calculation section compares the index image data with pattern data of the index for eye examination by patterning matching; and
means by which the calculation section calculates the evaluation parameter based on a comparison result by the pattern matching.

9. The ophthalmic data measuring apparatus according to claim 1, wherein the calculation section is constructed to estimate a high contrast visual acuity and/or a low contrast visual acuity of the eye to be examined by using a high contrast index for eye examination and/or a low contrast index for eye examination.

10. The ophthalmic data measuring apparatus according to claim 1, wherein with respect to the third means, the calculation section judges whether the evaluation parameter indicating visibility of an index for eye examination satisfies a previously specified reference, and estimates the visual acuity in accordance with a size of the index for eye examination corresponding to the evaluation parameter satisfying the reference.

11. The ophthalmic data measuring apparatus according to claim 10, wherein the calculation section further comprises:
means for obtaining data of an MTF (Modulation Transfer Function) indicating a transfer characteristic of the eye to be examined based on the lower order aberrations and the higher order aberrations; and
means for estimating a contrast sensitivity based on the obtained data of the MTF.

12. The ophthalmic data measuring apparatus according to claim 1, wherein with respect to the second means,
the calculation section obtains data of an MTF (Modulation Transfer Function) indicating a transfer characteristic of the eye to be examined based on the lower order aberrations and the higher order aberrations; and
with respect to the third means, the calculation section estimates a contrast sensitivity based on the obtained data of the MTF.

13. The ophthalmic data measuring apparatus according to claim 1, wherein the calculation section further comprises means for obtaining a pupil center position under the observation condition based on the received pupil data and for calculating a shift amount of the pupil center position to shift an analysis center.

14. The ophthalmic data measuring apparatus according to claim 1, wherein the calculation section further comprises means for storing one of or two or more of the visual acuity, the sensitivity, the correction data, and a simulation result into a memory or displaying them on a display section.

15. The ophthalmic data measuring apparatus according to claim 1, wherein the third means is constructed to estimate, as the optical characteristic, an MTF (Modulation Transfer Function) of the eye to be examined, and a point spread function (PSF).

16. The ophthalmic data measuring apparatus according to claim 1, wherein the calculation section further comprises
means for obtaining the appropriate correction data suitable for the eye to be examined by changing the lower order aberration corresponding to defocus in accordance with the evaluation parameter calculated by the second means and for simulating the visibility of an image by the eye to be examined at a time of correction based on the correction data to further calculate an evaluation parameter,
and estimates the visual acuity and/or the sensitivity at the time of correction.

17. The ophthalmic data measuring apparatus according to claim 1, wherein the calculation section further comprises
means for obtaining appropriate correction data suitable for the eye to be examined by changing the lower order aberration corresponding to an astigmatic component in accordance with the evaluation parameter calculated by the second means and for simulating the visibility of an image by the eye to be examined at a time of correction based on the correction data to further calculate an evaluation parameter,
and estimates the visual acuity and/or the sensitivity at the time of correction.

18. The ophthalmic data measuring apparatus according to claim 1, wherein the calculation section further comprises
fourth means for simulating a Landolt's ring based on the calculated correction data or a luminance distribution image of an arbitrary image, and storing the correction data and/or a simulation result into a memory or displaying it on a display section.

19. The ophthalmic data measuring apparatus according to claim 1, wherein with respect to the third means, in a case where a higher order spherical aberration or an unsymmetrical higher order coma aberration has a predetermined value or more, the calculation section changes the lower order aberration corresponding to defocus based on the evaluation parameter and obtains the appropriate correction data suitable for the eye to be examined.

20. The ophthalmic data measuring apparatus according to claim 1, wherein with respect to the third means, in a case where a higher order astigmatic aberration has a predetermined value or more, the calculation section changes the lower order aberration corresponding to an astigmatic component based on the evaluation parameter and obtains the appropriate correction data suitable for the eye to be examined.

21. The ophthalmic data measuring apparatus according to claim 1, wherein
with respect to the second means, the calculation section calculates a Strehl ratio as the evaluation parameter based on the obtained lower order aberrations and the higher order aberrations, and
with respect to the third means, the calculation section changes a predetermined lower order aberration to increase the Strehl ratio and calculates the appropriate correction data suitable for the eye to be examined.

22. The ophthalmic data measuring apparatus according to claim 1, wherein
with respect to the second means, the calculation section calculates a phase shift as the evaluation parameter based on the obtained lower order aberrations and the higher order aberrations, and
with respect to the third means, the calculation section changes the lower order aberration to decrease a phase shift and calculates the appropriate correction data suitable for the eye to be examined.

23. The ophthalmic data measuring apparatus according to claim 1, wherein the second means comprises:
means by which the calculation section forms data of an MTF (Modulation Transfer Function) indicating a transfer characteristic of the eye to be examined after correction based on the lower order aberrations and the higher order aberrations, and
means by which the calculation section calculates the evaluation parameter based on the formed data of the MTF.

24. The ophthalmic data measuring apparatus according to claim 1, wherein
with respect to the second means, the calculation section forms, as the evaluation parameter, a relational expression between a Strehl ratio and a phase shift based on the lower order aberrations and the higher order aberrations, and
with respect to the third means, the calculation section changes the lower order aberration to obtain a condition under which the Strehl ratio becomes maximum and the phase shift becomes substantially zero, and makes the lower order aberration at that time the appropriate correction data.

25. An ophthalmic data measurement program for causing a computer to execute:

a first step at which a calculation section obtains measurement data indicating a refractive power distribution of an eye to be examined and pupil data including a value of a pupil diameter of the eye to be examined or a pupil diameter image, and obtains lower order aberrations and higher order aberrations based on an observation condition parameter including the measurement data and the pupil data;
a second step at which the calculation section calculates an evaluation parameter indicating quality of visibility by the eye to be examined based on the observation condition parameter and/or the obtain lower order aberrations and the higher order aberrations; and
a third step at which in accordance with the calculated evaluation parameter, the calculation section estimates one of or two or more of a visual acuity, an optical characteristic and a sensitivity of the eye to be examined under an observation condition corresponding to an environment of a subjective eye, or calculates appropriate correction data suitable for the eye to be examined by changing the lower order aberration.

26. An ophthalmic data measurement program for causing a computer to execute:
a first step at which a calculation section receives measurement data indicating a refractive power distribution of an eye to be examined, and obtains lower order aberrations and higher order aberrations based on the measurement data;
a second step at which the calculation section calculates an evaluation parameter indicating quality of visibility by the eye to be examined based on the obtained lower order aberrations and the higher order aberrations; and
a third step at which the calculation section calculates appropriate correction data suitable for the eye to be examined by changing the lower order aberration in accordance with the calculated evaluation parameter.

27. An eye characteristic measuring apparatus comprising:
a first light source part to emit a light flux of a first wavelength;
a first illuminating optical system for performing illumination to condense the light flux from the first light source part on a vicinity of a retina of an eye to be examined;
a first light receiving optical system for receiving a part of the light flux reflected by and returning from the retina of the eye to be examined through a first conversion member to convert it into at least substantially 17 beams;
a first light receiving part for receiving the received light flux of the first light receiving optical system; and
a calculation section for receiving pupil data including a pupil image of the eye to be examined in a measurement environment, calculating a pupil diameter under the measurement environment based on the received pupil data, and obtaining an optical characteristic of the eye to be examined based on the calculated pupil diameter and an output signal from the first light receiving part.

* * * * *